(12) United States Patent
Inoue et al.

(10) Patent No.: US 8,877,351 B2
(45) Date of Patent: *Nov. 4, 2014

(54) ORGANOMETALLIC COMPLEX, AND LIGHTING APPARATUS, AND ELECTRONIC DEVICE USING THE ORGANOMETALLIC COMPLEX

(75) Inventors: Hideko Inoue, Atsugi (JP); Satoshi Seo, Kawasaki (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 793 days.

This patent is subject to a terminal disclaimer.

(21) Appl. No.: 12/489,602

(22) Filed: Jun. 23, 2009

(65) Prior Publication Data
US 2009/0322217 A1 Dec. 31, 2009

(30) Foreign Application Priority Data
Jun. 25, 2008 (JP) ................. 2008-166035

(51) Int. Cl.
| H01L 51/54 | (2006.01) |
| C09K 11/00 | (2006.01) |
| C07F 15/00 | (2006.01) |
| C09K 11/06 | (2006.01) |
| H01L 51/00 | (2006.01) |
| H05B 33/14 | (2006.01) |
| H01L 51/50 | (2006.01) |

(52) U.S. Cl.
CPC ............ *C07F 15/0033* (2013.01); *C09K 11/06* (2013.01); *C09K 2211/1007* (2013.01); *C09K 2211/1044* (2013.01); *C09K 2211/185* (2013.01); *H01L 51/0085* (2013.01); *H01L 51/5016* (2013.01); *H05B 33/14* (2013.01); Y10S 428/917 (2013.01)
USPC ........... 428/690; 428/917; 313/504; 313/506; 257/40; 257/101; 257/E51.044; 252/301.16; 544/255; 544/343

(58) Field of Classification Search
None
See application file for complete search history.

(56) References Cited

U.S. PATENT DOCUMENTS

| 7,238,806 | B2 | 7/2007 | Inoue et al. |
| 8,048,540 | B2 | 11/2011 | Inoue et al. |
| 8,455,111 | B2 | 6/2013 | Ohsawa et al. |
| 8,471,248 | B2 | 6/2013 | Schmidhalter et al. |
| 2003/0059646 | A1 | 3/2003 | Kamatani et al. |
| 2003/0068526 | A1 | 4/2003 | Kamatani et al. |
| 2006/0159955 | A1 | 7/2006 | Inoue et al. |
| 2007/0034854 | A1 | 2/2007 | Inoue et al. |
| 2007/0191587 | A1 | 8/2007 | Kanitz et al. |
| 2007/0216288 | A1 | 9/2007 | Lin et al. |
| 2007/0241667 | A1 | 10/2007 | Ohsawa et al. |
| 2007/0244320 | A1 | 10/2007 | Inoue et al. |
| 2008/0160345 | A1 | 7/2008 | Inoue et al. |
| 2013/0264556 | A1 | 10/2013 | Ohsawa et al. |

FOREIGN PATENT DOCUMENTS

| EP | 1873163 | A | 1/2008 |
| EP | 1939208 | A | 7/2008 |
| JP | 2005-298483 | | 10/2005 |
| JP | 2006-151887 | | 6/2006 |
| JP | 2007-091718 | A | 4/2007 |
| JP | 2007-522271 | A | 8/2007 |
| JP | 2007-284432 | A | 11/2007 |
| JP | 2008-179607 | A | 8/2008 |
| JP | 2011-511821 | | 4/2011 |
| KR | 2006-0036670 | A | 5/2006 |
| TW | 200844099 | | 11/2008 |

(Continued)

OTHER PUBLICATIONS

International Search Report (Application No. PCT/JP2009/061546) Dated Jul. 28, 2009.
Written Opinion (Application No. PCT/JP2009/061546) Dated Jul. 28, 2009.

(Continued)

*Primary Examiner* — Michael H Wilson
(74) *Attorney, Agent, or Firm* — Eric J. Robinson; Robinson Intellectual Property Law Office, P.C.

(57) ABSTRACT

Disclosed are an organometallic complex emitting red light with high color purity. An organometallic complex having a structure represented by the following general formula (G1) is provided.

(G1)

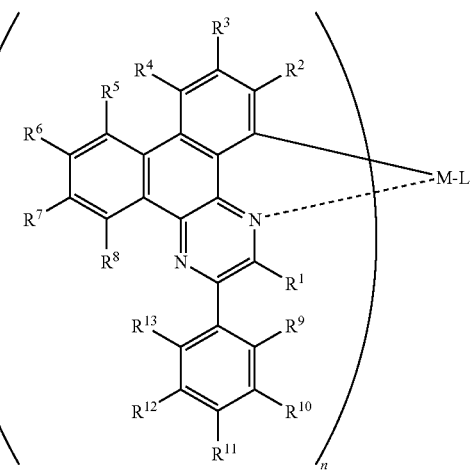

In the formula, of $R^1$ to $R^{13}$, at least one represents an alkyl group having 1 to 4 carbon atoms or an alkoxy group having 1 to 4 carbon atoms and the other or others represent hydrogen. M represents a central metal, which is a Group 9 or Group 10 element. L represents a monoanionic ligand, and n is 2 when the central metal is a Group 9 element or 1 when the central metal is a Group 10 element.

4 Claims, 15 Drawing Sheets

(56) References Cited

FOREIGN PATENT DOCUMENTS

| | | |
|---|---|---|
| TW | 200940554 | 10/2009 |
| TW | 200940678 | 10/2009 |
| WO | WO 2006/059802 | 6/2006 |
| WO | WO 2006/062144 | 6/2006 |
| WO | WO-2009/069535 | 6/2009 |
| WO | WO-2009/100991 | 8/2009 |

OTHER PUBLICATIONS

Jiun-Pey Duan et al., *New Iridium Complexes as Highly Efficient Orange-Red Emitters in Organic Light-Emittting Diodes*, Advanced Materials, vol. 15, No. 3, Feb. 5, 2003, pp. 224-228.

Peter J. Steel et al., *Cyclometallated Compounds V. Double Cyclopalladation of Diphenyl Pyrazines and Related Ligands*, Journal of Organometallic Chemistry, 395, 1990, pp. 359-373.

Search Report (Application No. 07024831.5) dated Mar. 26, 2008.

Taiwanese Office Action (Application No. 98121209) Dated Jan. 10, 2014.

ORGANOMETALLIC COMPLEX, AND LIGHTING APPARATUS, AND ELECTRONIC DEVICE USING THE ORGANOMETALLIC COMPLEX

TECHNICAL FIELD

The present invention relates to an organometallic complex. In particular, the present invention relates to an organometallic complex that enables luminescence to occur with energy of a triplet excited state. In addition, the present invention relates to a light-emitting element, a light-emitting device and an electronic device which use the organometallic complex.

BACKGROUND ART

An organic compound absorbs light, thereby producing an excited state. The organic compound undergoes this excited state; accordingly, luminescence or various reactions (such as photochemical reactions) may occur. Therefore, various applications of the organic compounds have been made.

A light-emitting element including an organic compound as a light-emitting substance has a simple structure in which a light-emitting layer containing the organic compound that is the light-emitting substance is provided between electrodes. This light-emitting element has attracted attention as a next-generation flat panel display element in terms of its characteristics such as thinness, lightness, high-speed response, and DC drive at low voltage. Further, a display including this light-emitting element is superior in contrast, image quality, and wide viewing angle.

The light-emitting element including an organic compound as a light-emitting substance has a mechanism of light emission, which is a carrier injection type: a voltage is applied between the electrodes where the light-emitting layer is interposed, electrons and holes injected from the electrodes recombine to produce an excited state of the light-emitting substance, and then light is emitted when the light-emitting substance returns to a ground state from the excited state. As in the case of the photoexcitation, types of the excited state of organic compounds include a singlet excited state (S*) and a triplet excited state (T*). Furthermore, it is thought that the ratio of S* to T* in a light-emitting element is statistically 1:3.

At room temperature, a compound that enables luminescence to occur with energy of a singlet excited state (hereinafter, referred to as a fluorescent compound) exhibits only luminescence from the singlet excited state (fluorescence), not luminescence from the triplet excited state (phosphorescence). Accordingly, the internal quantum efficiency (the ratio of generated photons to injected carriers) of a light-emitting element including a fluorescent compound is assumed to have a theoretical limit of 25% based on the ratio, S*:T*=1:3.

On the other hand, with a light-emitting element including a compound that enables luminescence to occur with energy of a triplet excited state (hereinafter, referred to as a phosphorescent compound), the internal quantum efficiency can be improved to 75 to 100% in theory; namely, the emission efficiency can be 3 to 4 times as high as that of a light-emitting element including a fluorescent compound. Therefore, light-emitting elements including phosphorescent compounds have been actively developed in recent years in order to achieve a highly-efficient light-emitting element, (e.g., see Non-patent Document 1). An organometallic complex that contains iridium or the like as a central metal is particularly attracting attention as a phosphorescent compound because of its high phosphorescence quantum efficiency.

PRIOR ART DOCUMENT

Non-Patent Document

[Non-Patent Document 1]
Jiun-Pey Duan et. al., *Advanced Materials*, 2003, vol. 15, No. 3, pp. 224-228

DISCLOSURE OF INVENTION

However, in the present state, the number of kinds of such phosphorescent compounds is small. Further, since the organometallic complex disclosed in Non-Patent Document 1 emits orange-red light, which makes the purity of red color poor, this organometallic complex is disadvantage in color reproducibility for application to a full-color display or the like. In contrast, in the case of an organometallic complex that emits dark red light, that is, light having an extremely long emission wavelength, the organometallic complex is advantageous in terms of color reproducibility. In this case, however, the organometallic complex has lower luminous efficiency (cd/A).

In view of the foregoing, an object of the present invention is to provide an organometallic complex which emits red light with high color purity and high emission efficiency. Moreover, an object of the present invention is to provide a light-emitting element which exhibits red light emission with high color purity and has high emission efficiency.

As a result of intense study in order to achieve the above objects, the present inventors have found that an organometallic complex can be formed by ortho-metalation of a dibenzo[f h]quinoxaline derivative represented by a general formula (G0) below with a metal ion of Group 9 or Group 10 of the periodic table. Further, the present inventors have also found that the organometallic complex tends to exhibit inter-system crossing and can efficiently exhibit phosphorescence. Furthermore, the present inventors have found that the organometallic complex emits light of favorable red color.

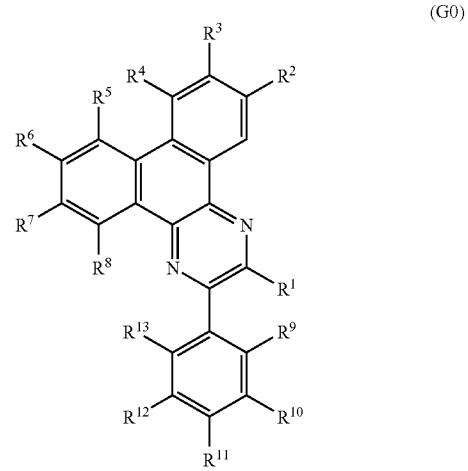

(G0)

In the formula, of $R^1$ to $R^{13}$, at least one represents an alkyl group having 1 to 4 carbon atoms or an alkoxy group having 1 to 4 carbon atoms and the other or others represent hydrogen. When two or more of $R^1$ to $R^{13}$ represent alkyl or alkoxy groups each having 1 to 4 carbon atoms, the alkyl or alkoxy groups may be bonded to form a ring or rings.

According to an embodiment of the present invention, an organometallic complex having a partial structure represented by the following general formula (G1') is provided.

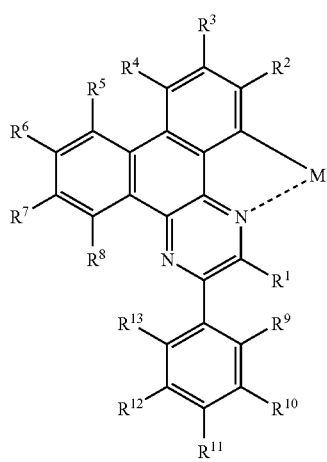

(G1')

In the formula, of $R^1$ to $R^{13}$, at least one represents an alkyl group having 1 to 4 carbon atoms or an alkoxy group having 1 to 4 carbon atoms and the other or others represent hydrogen. When two or more of $R^1$ to $R^{13}$ represent alkyl or alkoxy groups each having 1 to 4 carbon atoms, the alkyl or alkoxy groups may be bonded to form a ring or rings. In addition, M represents a central metal, which is a Group 9 or Group 10 element.

In the dibenzo[f,h]quinoxaline derivative represented by the above general formula (G0), $R^1$ is preferably hydrogen in view of synthesis yield, in which case the steric hindrance of the dibenzo[f,h]quinoxaline derivative is reduced so that ortho-metalation of the dibenzo[f,h]quinoxaline derivative with a metal ion is facilitated. In addition, it is preferable that $R^4$, $R^5$, $R^8$, $R^9$, and $R^{13}$ be individually hydrogen in view of ease of synthesis. In this case, the organometallic complex of the present invention has a partial structure represented by a general formula (G2') below. Thus, a preferable embodiment of the present invention is an organometallic complex having the partial structure represented by the following general formula (G2').

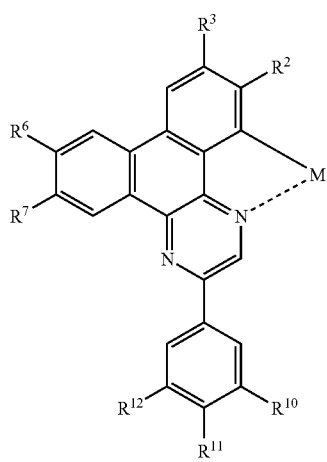

(G2')

In the formula, of $R^2$, $R^3$, $R^6$, $R^7$, $R^{10}$, $R^{11}$, and $R^{12}$, at least one represents an alkyl group having 1 to 4 carbon atoms or an alkoxy group having 1 to 4 carbon atoms and the other or others represent hydrogen. When two or more of $R^2$, $R^3$, $R^6$, $R^7$, $R^{10}$, $R^{11}$, and $R^{12}$ represent alkyl or alkoxy groups each having 1 to 4 carbon atoms, the alkyl or alkoxy groups may be bonded to form a ring or rings. In addition, M represents a central metal, which is a Group 9 or Group 10 element.

In the above general formula (G2'), it is preferable that $R^2$, $R^3$, $R^6$, and $R^7$ be individually hydrogen in view of further ease of synthesis. Accordingly, a more preferable embodiment of the present invention is an organometallic complex having a partial structure represented by the following general formula (G3').

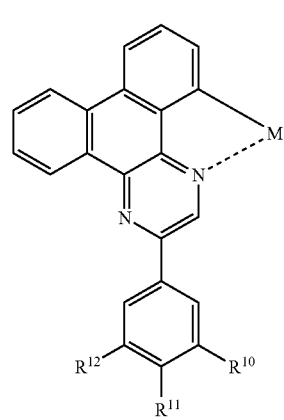

(G3')

In the formula, of $R^{10}$, $R^{11}$, and $R^{12}$, at least one represents an alkyl group having 1 to 4 carbon atoms or an alkoxy group having 1 to 4 carbon atoms and the other or others represent hydrogen. When two or more of $R^{10}$, $R^{11}$, and $R^{12}$ represent alkyl or alkoxy groups each having 1 to 4 carbon atoms, the alkyl or alkoxy groups may be bonded to form a ring or rings. In addition, M represents a central metal, which is a Group 9 or Group 10 element.

Here, as a specific structure of the organometallic complex having the partial structure represented by the above general formula (G1'), an organometallic complex represented by a general formula (G1) below is preferable in view of ease of synthesis.

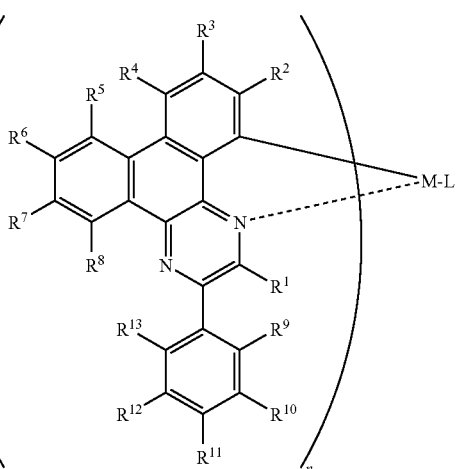

(G1)

In the formula, of $R^1$ to $R^{13}$, at least one represents an alkyl group having 1 to 4 carbon atoms or an alkoxy group having 1 to 4 carbon atoms and the other or others represent hydrogen. When two or more of $R^1$ to $R^{13}$ represent alkyl or alkoxy groups each having 1 to 4 carbon atoms, the alkyl or alkoxy groups may be bonded to form a ring or rings. Further, M represents a central metal, which is a Group 9 or Group 10 element, and L represents a monoanionic ligand. In addition, n is 2 when the central metal is a Group 9 element or 1 when the central metal is a Group 10 element.

Further, as a specific structure of the organometallic complex having the structure represented by the above general formula (G1), an organometallic complex represented by a general formula (G2) below is preferable in view of ease of synthesis.

(G2)

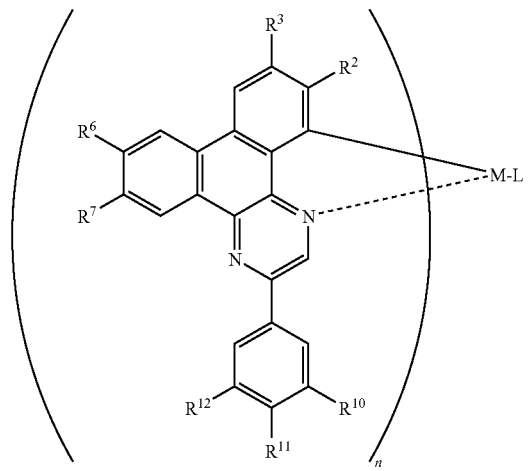

In the formula, of $R^2$, $R^3$, $R^6$, $R^7$, $R^{10}$, $R^{11}$, and $R^{12}$, at least one represents an alkyl group having 1 to 4 carbon atoms or an alkoxy group having 1 to 4 carbon atoms and the other or others represent hydrogen. When two or more of $R^2$, $R^3$, $R^6$, $R^7$, $R^{10}$, $R^{11}$, and $R^{12}$ represent alkyl or alkoxy groups each having 1 to 4 carbon atoms, the alkyl or alkoxy groups may be bonded to form a ring or rings. Further, M represents a central metal, which is a Group 9 or Group 10 element, and L represents a monoanionic ligand. In addition, n is 2 when the central metal is a Group 9 element or 1 when the central metal is a Group 10 element.

Further, as a more specific structure of the organometallic complex having the structure represented by the above general formula (G2), an organometallic complex represented by a general formula (G3) below is preferable in view of ease of synthesis.

(G3)

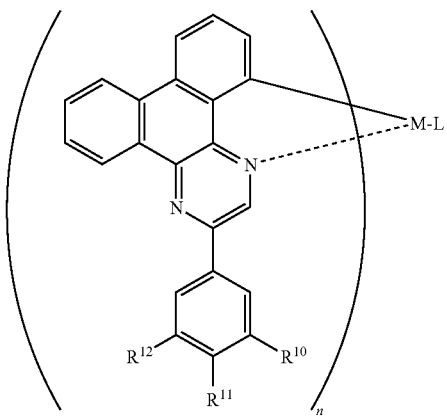

In the formula, of $R^{10}$, $R^{11}$, and $R^{12}$, at least one represents an alkyl group having 1 to 4 carbon atoms or an alkoxy group having 1 to 4 carbon atoms and the other or others represent hydrogen. When two of $R^{10}$, $R^{11}$, and $R^{12}$ represent alkyl or alkoxy groups each having 1 to 4 carbon atoms, the alkyl or alkoxy groups may be bonded to form a ring. Further, M represents a central metal, which is a Group 9 or Group 10 element, and L represents a monoanionic ligand. In addition, n is 2 when the central metal is a Group 9 element or 1 when the central metal is a Group 10 element.

In addition, the above-mentioned monoanionic ligand L is preferably any one of a monoanionic bidentate chelate ligand having a β-diketone structure, a monoanionic bidentate chelate ligand having a phenolic hydroxyl group, or a monoanionic bidentate chelate ligand in which two ligand elements are both nitrogen, because these ligands have high coordinating ability. More preferably, the monoanionic ligand L represents a monoanionic ligand represented by structural formulae (L1) to (L9) below. Since these ligands have high coordinating ability and can be obtained at low price, they are useful.

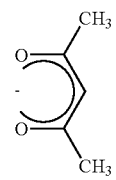

(L1)

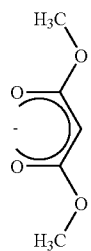

(L2)

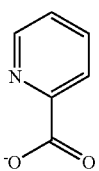

(L3)

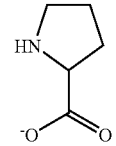

(L4)

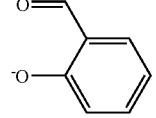

(L5)

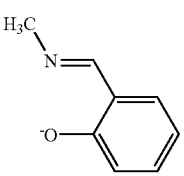

(L6)

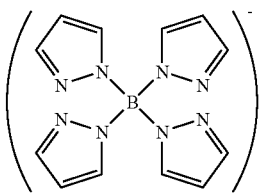

(L7)

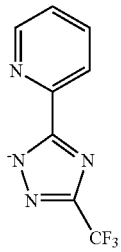

(L8)

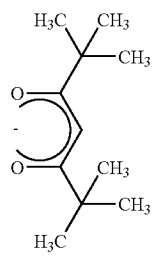

(L9)

Further, in order to obtain phosphorescence more efficiently, a heavy metal is preferable as the central metal in terms of heavy atom effect. Thus, in the present invention, the central metal M of any of the above-described organometallic complexes of the present invention is preferably iridium or platinum. Among them, iridium is particularly preferable, in which case heat resistance of the organometallic complex can be improved.

A coordination structure including ortho-metalation of the dibenzo[f,h]quinoxaline derivative represented by the general formula (G0) with a metal ion greatly contributes to the function of phosphorescence of the organometallic complex having the partial structure represented by any of the above general formulae (G1') to (G3') (inclusive of the organometallic complexes represented by the above general formulae (G1) to (G3)).

In addition, any of the organometallic complexes of the present invention can exhibit phosphorescence; in other words, it enables luminescence to occur with energy of a triplet excited state. Accordingly, any of the organometallic complexes is applied to a light-emitting element to achieve higher efficiency and thus very effective. Therefore, according to the present invention, a light-emitting element including any of the above-described organometallic complexes as a light-emitting substance is also provided.

It is preferable that the light-emitting element include a light-emitting layer between a pair of electrodes and that the light-emitting layer includes any of the organometallic complexes of the present invention and a substance (i.e., a host) used for dispersion of the organometallic complex.

Further, since the thus obtained light-emitting element of the present invention can achieve high emission efficiency, a light-emitting device (an image display device or a light-emitting device) using this light-emitting element as a light-emitting element can achieve reduced power consumption as well. Accordingly, the present invention also covers a light-emitting device and an electronic device each including the light-emitting element of the present invention.

A light-emitting device of the present invention includes a light-emitting element that has a light-emitting layer including any of the above organometallic complexes between a pair of electrodes and a control unit configured to control light emission of the light-emitting element. Note that the category of a light-emitting device in this specification includes an image display device or a light-emitting device using a light-emitting element. Further, the category of the light-emitting device of the present invention includes a module including a substrate provided with a light-emitting element, to which a connector such as a tape automated bonding (TAB) tape such as an anisotropic conductive film or a tape carrier package (TCP) is attached; a module in which an end of a connector is provided with a printed wiring board; and a module in which an integrated circuit (IC) is directly mounted on a substrate provided with a light-emitting element by a chip on glass (COG) method.

Further, an electronic device of the present invention includes a display portion, and the display portion includes the above-described light-emitting element and a control unit configured to control light emission of the light-emitting element.

With any of the organometallic complexes of the present invention, red light emission with high color purity can be obtained. Further, any of the organometallic complexes of the present invention have high emission efficiency. Furthermore, by fabrication of a light-emitting element using any of the organometallic complexes of the present invention, a light-emitting element that can exhibit red light emission with high color purity and has high emission efficiency can be obtained.

BEST MODE FOR CARRYING OUT THE INVENTION

Figure 1:
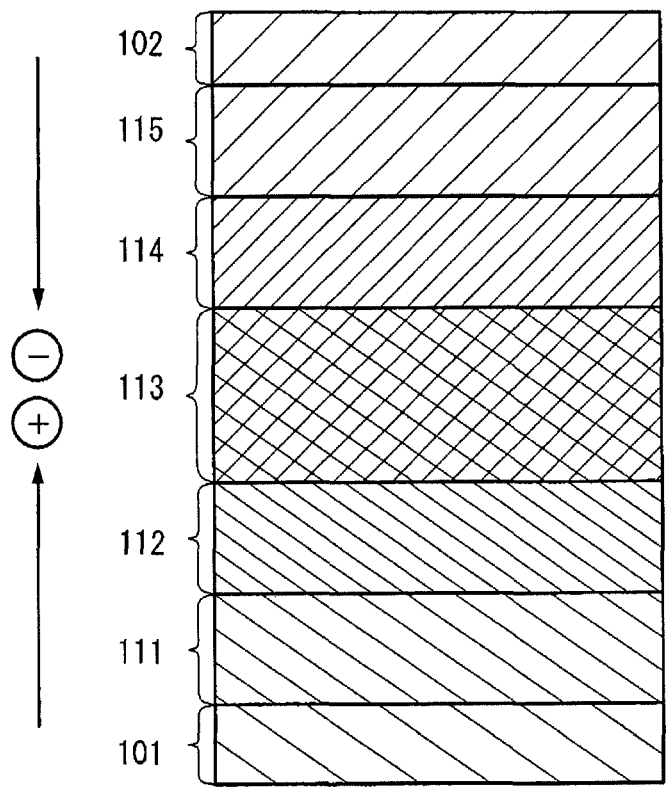
FIG. 1 illustrates a light-emitting element according to an embodiment of the present invention.

Hereinafter, embodiments of the present invention will be described in detail with reference to the accompanying drawings. Note that the present invention is not limited to the description below, and it is easily understood by those skilled in the art that a variety of changes and modifications can be made without departing from the spirit and scope of the present invention. Therefore, the present invention should not be interpreted as being limited to the content of the embodiments described below.

Embodiment 1

In Embodiment 1, organometallic complexes of the present invention will be described.

《《Synthesis Method of Dibenzo[f,h]quinoxaline Derivative Represented by General Formula (G0)》》

By ortho-metalation of the dibenzo[f,h]quinoxaline derivative represented by the general formula (G0) below with a metal ion of Group 9 or Group 10, an organometallic complex of the present invention is formed.

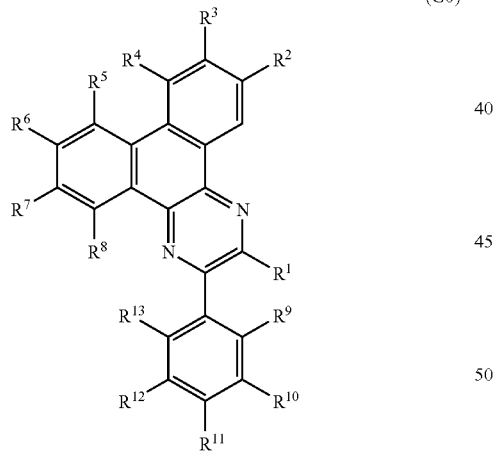

(G0)

In the formula, of $R^1$ to $R^{13}$, at least one represents an alkyl group having 1 to 4 carbon atoms or an alkoxy group having 1 to 4 carbon atoms and the other or others represent hydrogen. When two or more of $R^1$ to $R^{13}$ represent alkyl or alkoxy groups each having 1 to 4 carbon atoms, the alkyl or alkoxy groups may be bonded to form a ring or rings.

Hereinafter, a synthesis method of the dibenzo[f,h]quinoxaline derivative represented by the general formula (G0) is described separately for each of the case where $R^1$ in the general formula (G0) is an alkyl group having 1 to 4 carbon atoms or an alkoxy group having 1 to 4 carbon atoms (a general formula (G0-1) below) and the case where $R^1$ is hydrogen (a general formula (G0-2) below).

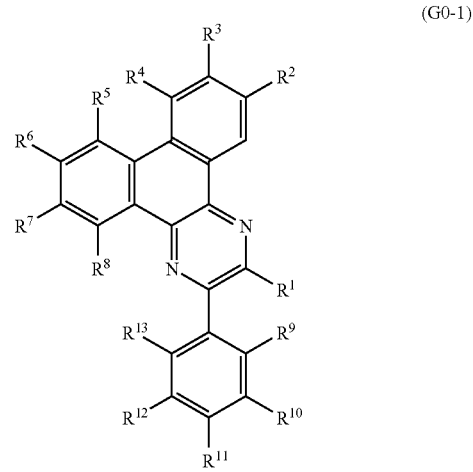

(G0-1)

In the formula, of $R^1$ to $R^{13}$, at least one represents an alkyl group having 1 to 4 carbon atoms or an alkoxy group having 1 to 4 carbon atoms and the other or others represent hydrogen. When two or more of $R^1$ to $R^{13}$ represent alkyl or alkoxy groups each having 1 to 4 carbon atoms, the alkyl or alkoxy groups may be bonded to form a ring or rings.

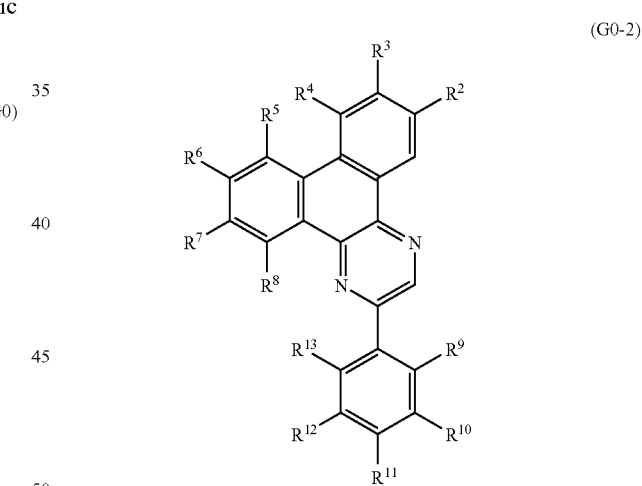

(G0-2)

In the formula, of $R^2$ to $R^{13}$, at least one represents an alkyl group having 1 to 4 carbon atoms or an alkoxy group having 1 to 4 carbon atoms and the other or others represent hydrogen. When two or more of $R^2$ to $R^{13}$ represent alkyl or alkoxy groups each having 1 to 4 carbon atoms, the alkyl or alkoxy groups may be bonded to form a ring or rings.

First, the dibenzo[f,h]quinoxaline derivative represented by the general formula (G0-1) can be synthesized according to a simple synthesis scheme as described below. For example, as illustrated in the scheme (a) below, the dibenzo [f,h]quinoxaline derivative can be obtained by reaction of a diaminophenanthrene compound (A1) and a diketone compound (A2).

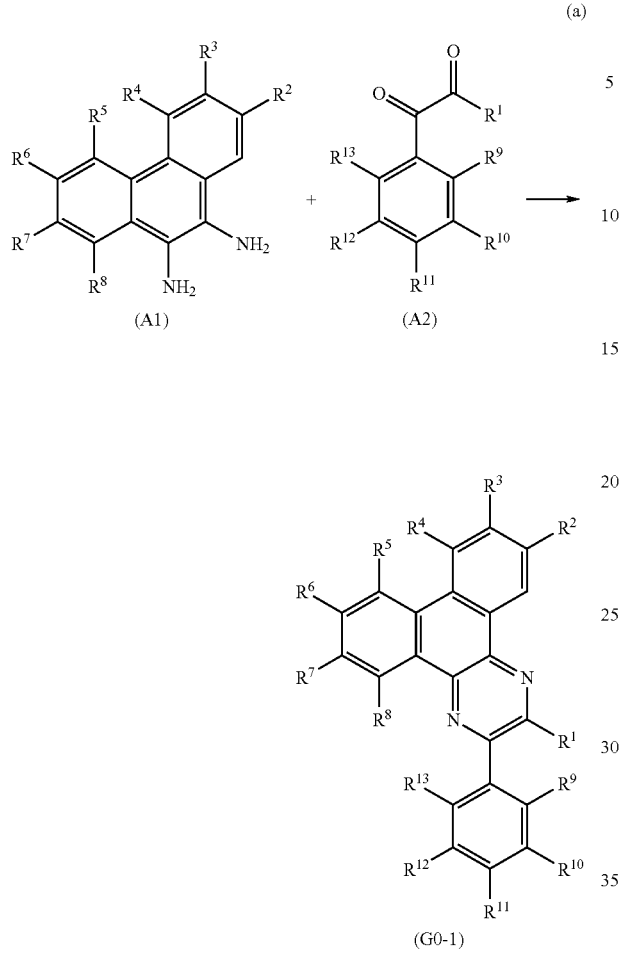

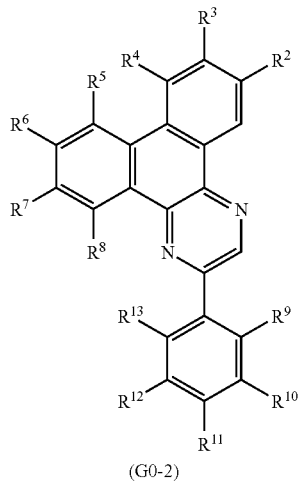

Alternatively, as illustrated in the scheme (a″) below, the dibenzo[f,h]quinoxaline derivative represented by the general formula (G0-2) can be obtained as follows: a diketone compound (A1″) and a diamine compound (A2″) react to give a dibenzo[f,h]quinoxaline derivative (G0-2′), and further, the dibenzo[f,h]quinoxaline derivative (G0-2′) thus obtained and aryllithium or an aryl magnesium bromide compound (A3) react.

On the other hand, as illustrated in the scheme (a′) below, the dibenzo[f,h]quinoxaline derivative represented by the general formula (G0-2) can be obtained by reaction of a diaminophenanthrene compound (A1′) and a diketone compound (A2′).

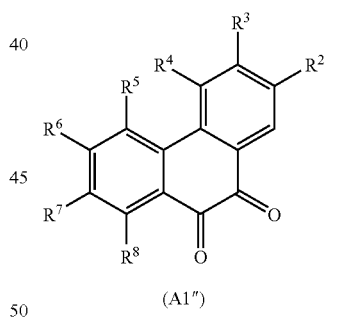

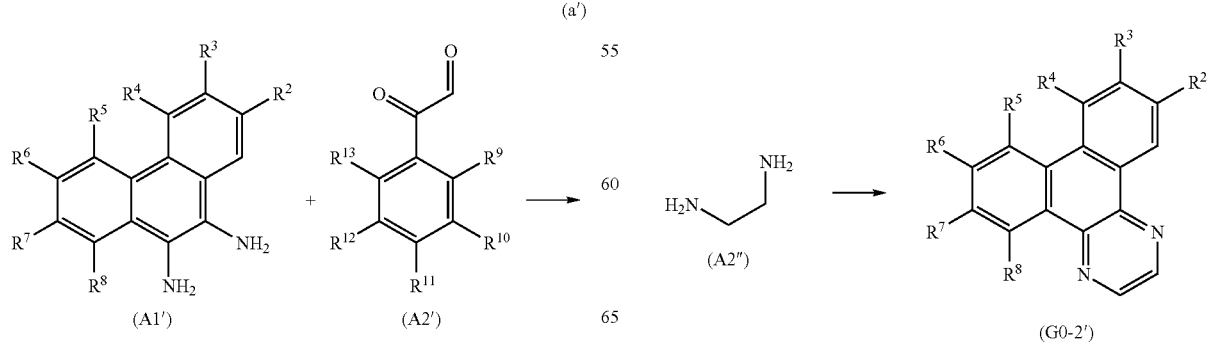

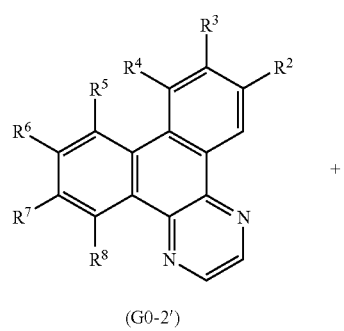

(G0-2')

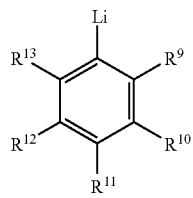

or

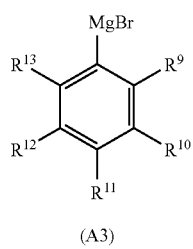

(A3)

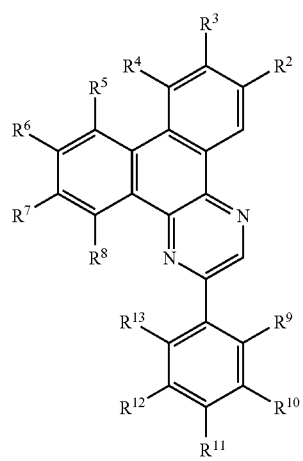

(G0-2)

Further alternatively, as illustrated in the scheme (a''') below, the dibenzo[f,h]quinoxaline derivative represented by the general formula (G0-2) can be obtained as follows: the dibenzo[f,h]quinoxaline derivative represented by the general formula (G0-2') and a halogenating agent react to give a halide (G0-2") of the dibenzo[f,h]quinoxaline derivative, and further, the thus obtained halide (G0-2") of the dibenzo[f,h]quinoxaline derivative and boronic acid with arene (A3') are coupled. Note that X in the formula represents a halogen element.

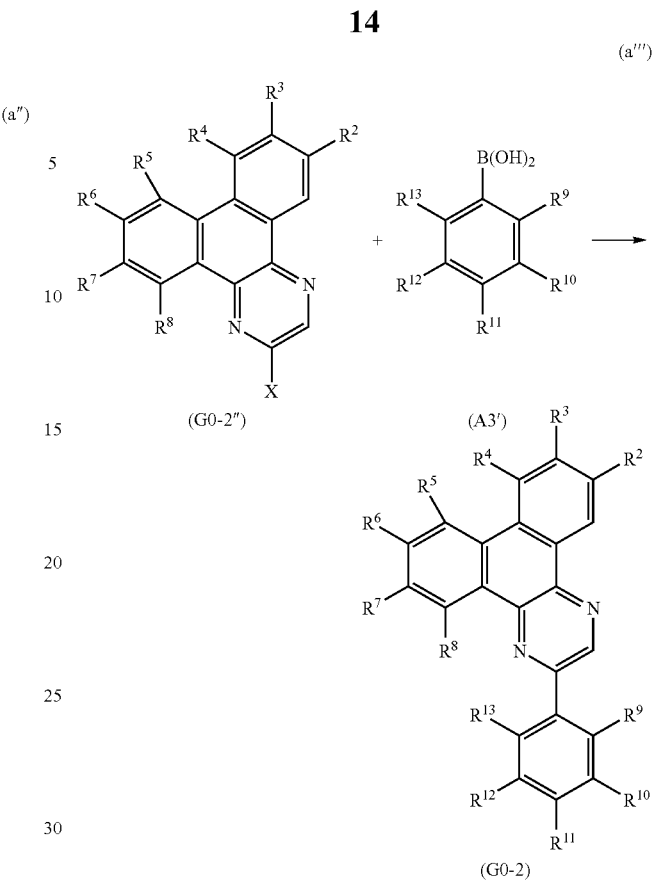

As the above compounds (A1), (A2), (A3), (A1'), (A2'), (A3'), (A1"), and (A2"), a variety of compounds are available commercially or can be synthesized. Therefore, there are many variations, which can be synthesized, in the dibenzo[f,h]quinoxaline derivative represented by the above-described general formula (G0).

《Synthesis Method of Organometallic Complex of Present Invention Having Partial Structure Represented by General Formula (G1')》

Next, an organometallic complex of the present invention which is formed by ortho-metalation of the dibenzo[f,h]quinoxaline derivative represented by the general formula (G0), that is, the organometallic complex having the partial structure represented by the following general formula (G1') will be described.

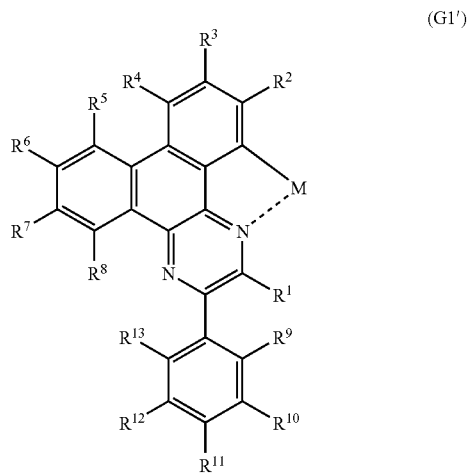

In the formula, of $R^1$ to $R^{13}$, at least one represents an alkyl group having 1 to 4 carbon atoms or an alkoxy group having 1 to 4 carbon atoms and the other or others represent hydrogen. When two or more of $R^1$ to $R^{13}$ represent alkyl or alkoxy groups each having 1 to 4 carbon atoms, the alkyl or alkoxy groups may be bonded to form a ring or rings. In addition, M represents a central metal, which is a Group 9 or Group 10 element.

First, as illustrated in the synthesis scheme (b) below, the dibenzo[f,h]quinoxaline derivative represented by the general formula (G0) and a compound of Group 9 or Group 10 metal which contains halogen (e.g., a metal halide or a metal complex) are heated in an appropriate solvent, whereby a dinuclear complex (B) having the partial structure represented by the general formula (G1') which is one of the organometallic complexes of the present invention can be obtained. Examples of compounds of Group 9 or Group 10 metal which contain halogen include, but not limited to, rhodium chloride hydrate, palladium chloride, iridium chloride hydrate, iridium chloride hydrochloride hydrate, potassium tetrachloroplatinate(II), and the like. Note that, in the synthesis scheme (b), M represents a Group 9 or Group 10 element and X represents a halogen element. In addition, n is 2 when M is a Group 9 element, or 1 when M is a Group 10 element.

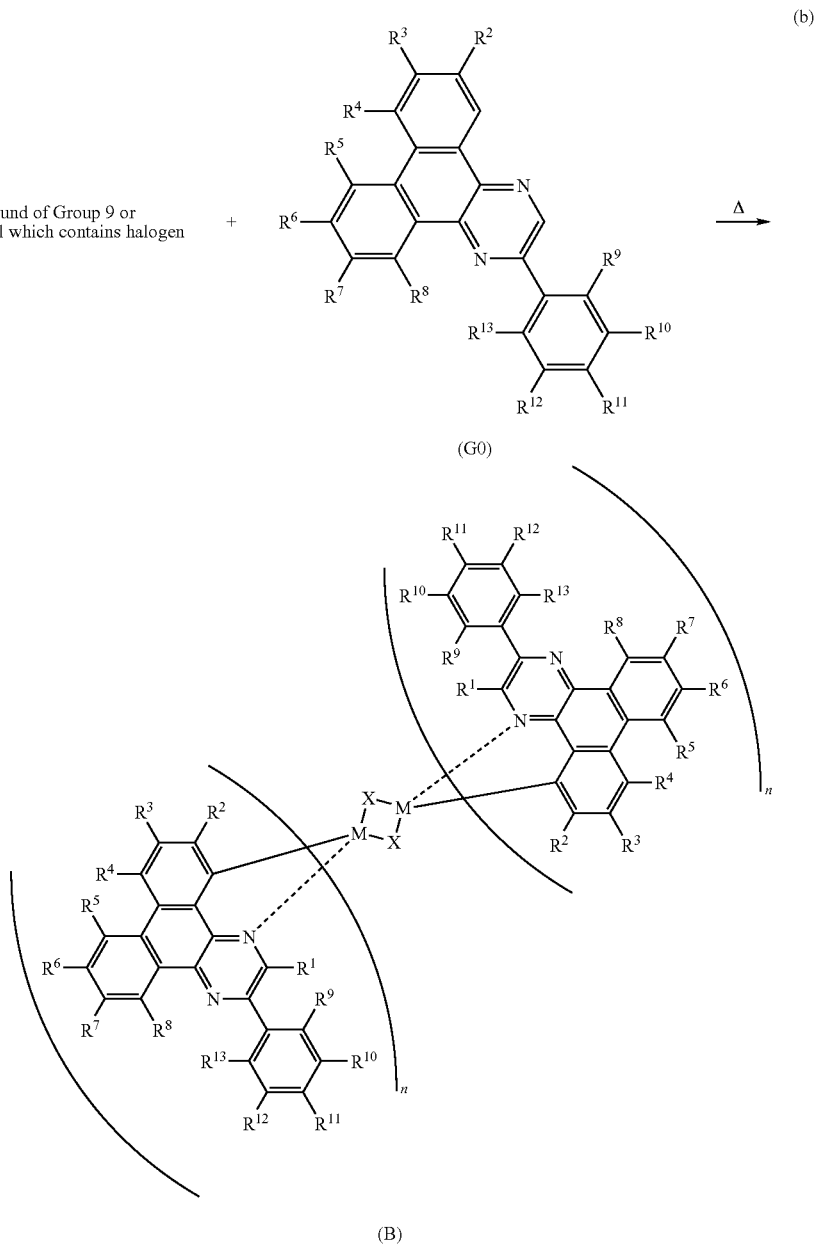

Furthermore, as illustrated in the synthesis scheme (c) below, the dinuclear complex (B) and the dibenzo[f,h]quinoxaline derivative represented by the general formula (G0) are heated at a high temperature of about 200° C. in a high boiling solvent such as glycerol, whereby an organometallic complex (C) having the partial structure represented by the general formula (G1') which is one of the organometallic complexes of the present invention can be synthesized. Further, as illustrated in the synthesis scheme (c') below, the dinuclear complex (B) and a compound capable of ortho-metalation (more generally, a compound capable of cyclometalation) such as phenylpyridine are heated at a high temperature of about 200° C. in a high boiling solvent such as glycerol, whereby an organometallic complex having the partial structure represented by the general formula (G1') which is one of the organometallic complexes of the present invention can be synthesized. Note that, in each of the synthesis schemes (c) and (c'), M represents a Group 9 or Group 10 element and X represents a halogen element. In addition, n is 2 when M is a Group 9 element, or 1 when M is a Group 10 element.

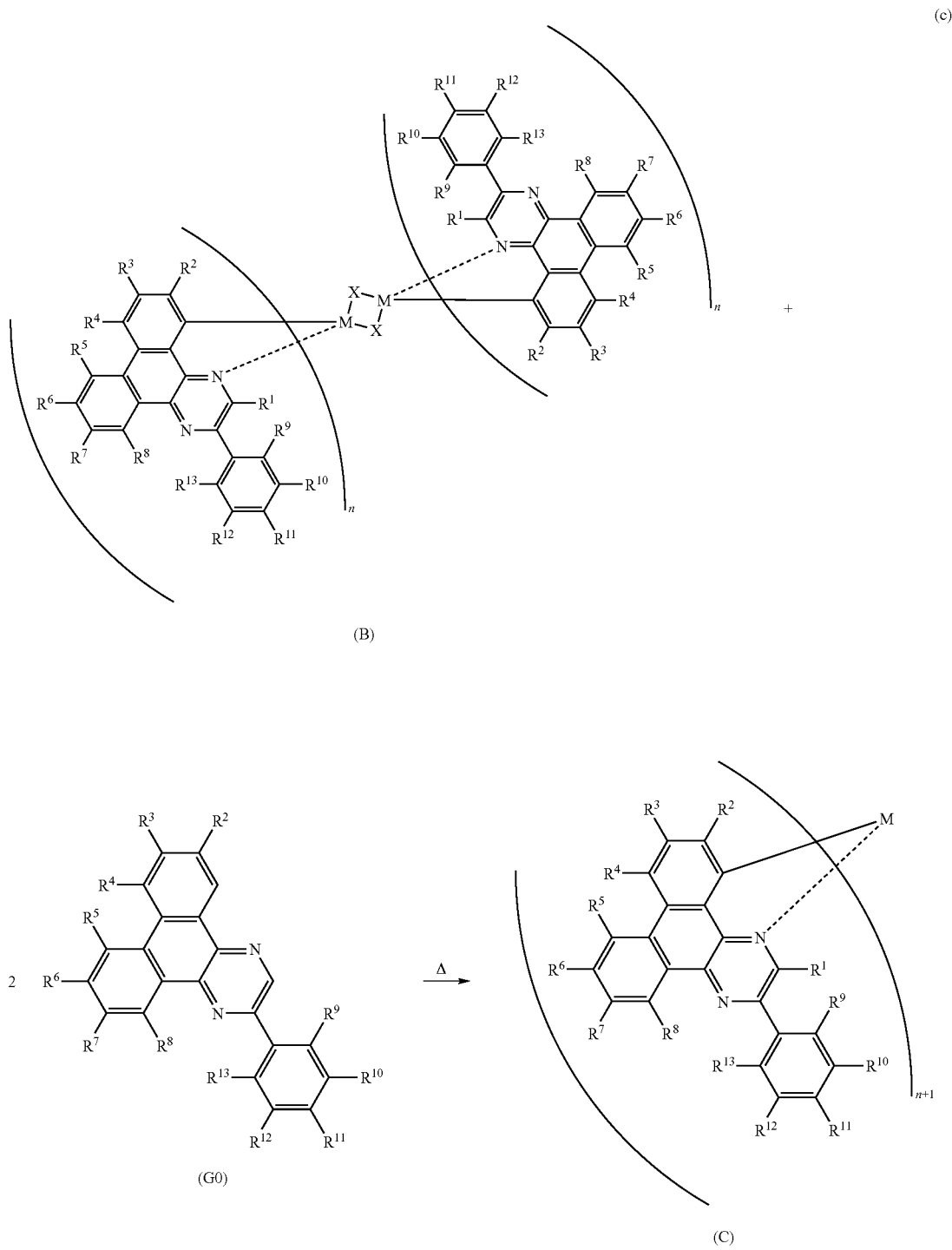

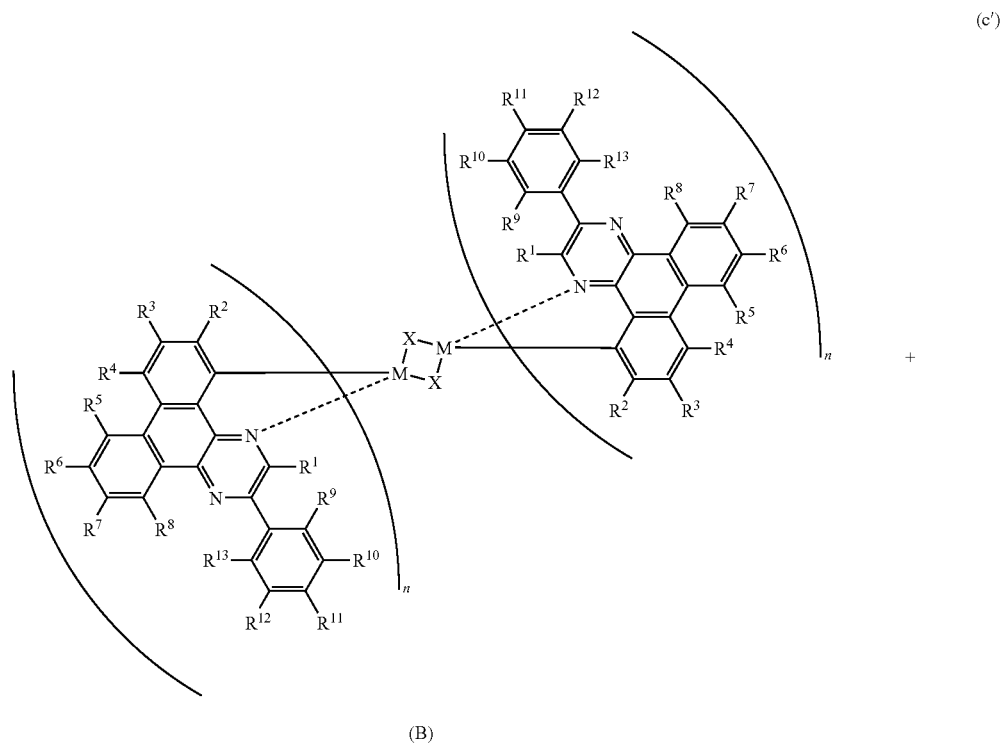
(B)
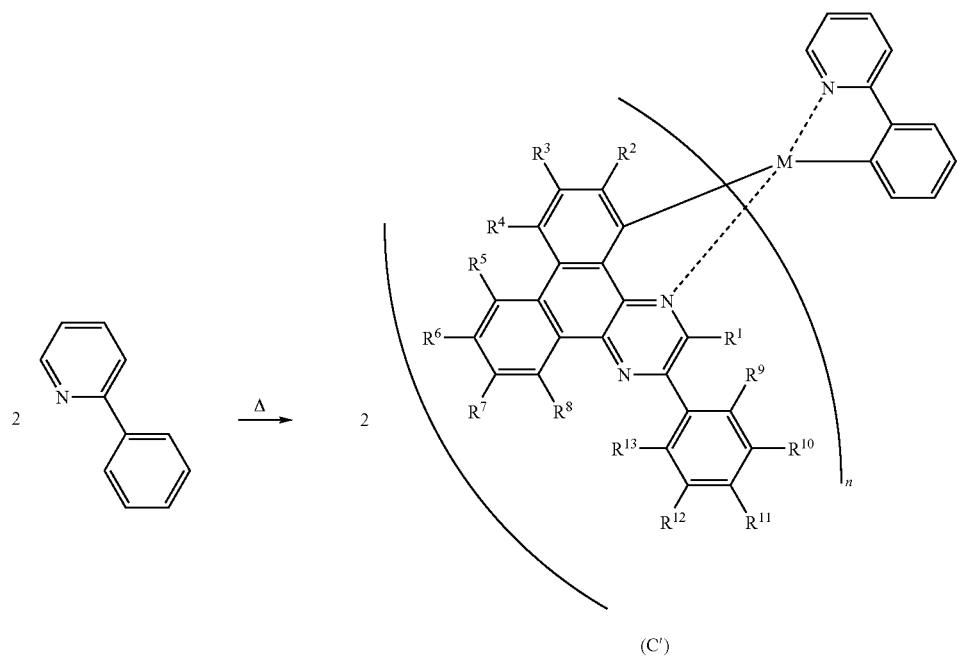
(C')

《《Synthesis Method of Organometallic Complex of Present Invention Having Structure Represented by General Formula (G1)》》

Here, the organometallic complex represented by the general formula (G1) below, which is a preferable specific example of the above organometallic complex having thepartial structure represented by the above-described general formula (G1'), will be described.

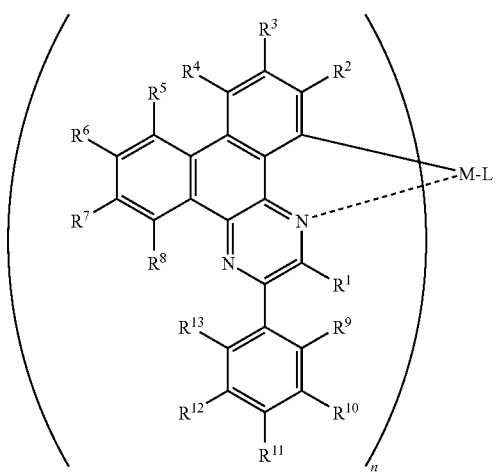

(G1)

In the formula, of $R^1$ to $R^{13}$, at least one represents an alkyl group having 1 to 4 carbon atoms or an alkoxy group having 1 to 4 carbon atoms and the other or others represent hydrogen. When two or more of $R^1$ to $R^{13}$ represent alkyl or alkoxy groups each having 1 to 4 carbon atoms, the alkyl or alkoxy groups may be bonded to form a ring or rings. Further, M represents a central metal, which is a Group 9 or Group 10 element, and L represents a monoanionic ligand. In addition, n is 2 when the central metal is a Group 9 element or 1 when the central metal is a Group 10 element.

The organometallic complex of the present invention which is represented by the above general formula (G1) can be synthesized according to the synthesis scheme (c") below. In other words, the organometallic complex of the present invention which is represented by the above general formula (G1) can be obtained as follows: the dinuclear complex (B) obtained according to the above synthesis scheme (b) and HL which is a material of the monoanionic ligand L react, and a proton of HL is eliminated and coordinated to the central metal M. Note that, in the synthesis scheme (c"), M represents a Group 9 or Group 10 element, and X represents a halogen element. In addition, n is 2 when M is a Group 9 element, or 1 when M is a Group 10 element.

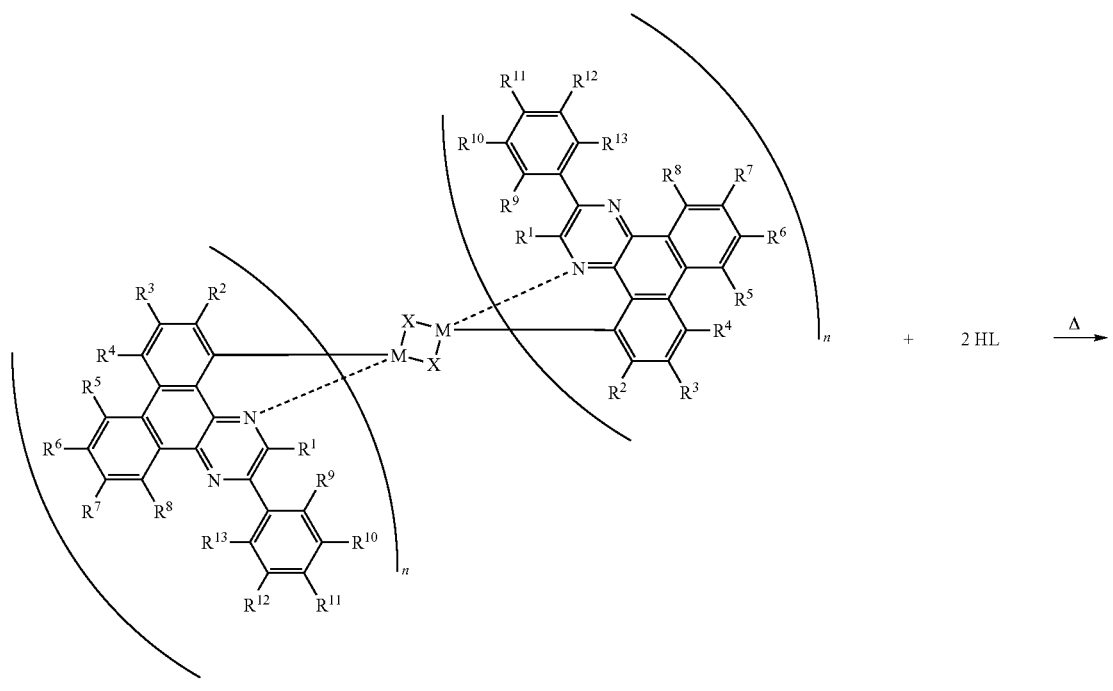

(B)

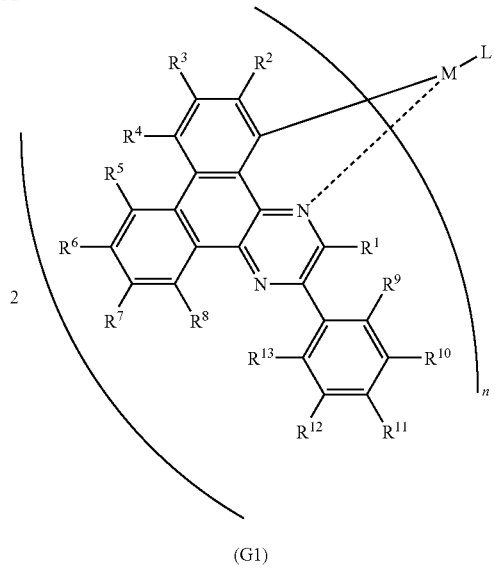

(G1)

《《Specific Structural Formulae of Organometallic Complex of Present Invention Having Partial Structure Represented by General Formula (G1') and Organometallic Complex of Present Invention Represented by General Formula (G1)》》

Next, specific structures of the organometallic complex of the present invention which has a partial structure represented by the general formula (G1') and the organometallic complex represented by the general formula (G1) will be disclosed.

First, the central metal M is selected from Group 9 elements and Group 10 elements and is preferably iridium(III) or platinum(II) in terms of emission efficiency. In particular, use of iridium(III) is preferable because of its thermal stability.

Next, a ligand portion P surrounded by dashed lines in each of the general formulae (G1') and (G1) below will be described. Note that, as described above, M represents a Group 9 or Group 10 element, and L represents a monoanionic ligand (specific examples are described later). In addition, n is 2 when M is a Group 9 element, or 1 when M is a Group 10 element.

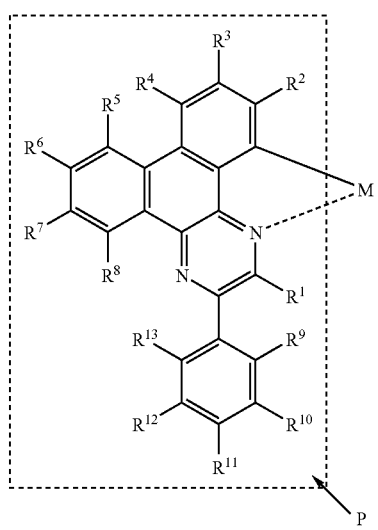

(G1')

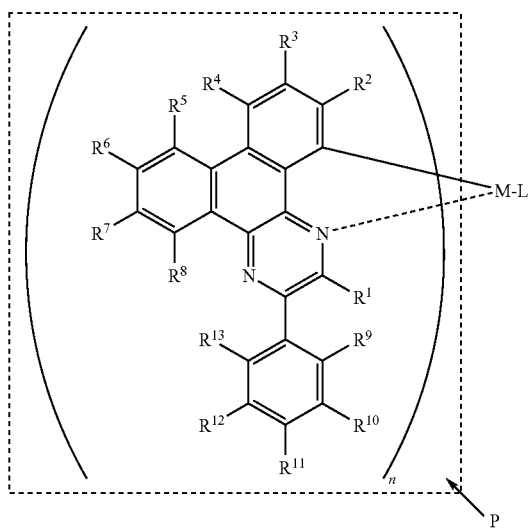

(G1)

As specific examples of the substituent $R^1$, there is an alkyl group such as a methyl group, an ethyl group, an isopropyl group, or a tert-butyl group, and an alkoxy group such as a methoxy group, an ethoxy group, an isopropoxy group, or a tert-butoxy group. Note that $R^1$ is preferably hydrogen in view of synthesis yield, in which case steric hindrance is reduced so that ortho-metalation of ligand portion P with a metal ion is facilitated.

As specific examples of substituents $R^2$ to $R^8$, there are hydrogen, an alkyl group such as a methyl group, an ethyl group, an isopropyl group, or a tert-butyl group, an alkoxy group such as a methoxy group, an ethoxy group, an isopropoxy group, or a tert-butoxy group, and an acyl group such as an acetyl group. Further, when $R^4$ and $R^5$ are bonded to form a ring, a methylene group or an ethylene group is formed, for example. Further, when $R^3$ and $R^4$ are bonded to form a ring or when $R^5$ and $R^6$ are bonded to form a ring, a methylenedioxy group or an ethylenedioxy group is formed, for example.

As specific examples of substituents $R^9$ to $R^3$, there is an alkyl group such as a methyl group, an ethyl group, an isopropyl group, or a tert-butyl group, and an alkoxy group such as a methoxy group, an ethoxy group, an isopropoxy group, or a tert-butoxy group. Further, when any of $R^1$ and $R^9$ are bonded to form a ring, a methylene group is formed, for example. Further, when $R^9$ and $R^{10}$ are bonded to form a ring or when $R^{10}$ and $R^{11}$ are bonded to form a ring (or when $R^{11}$ and $R^{12}$ are bonded to form a ring or when $R^{12}$ and $R^{13}$ are bonded to form a ring), a methylenedioxy group or the like is formed, for example.

Next, the monoanionic ligand L in the above general formula (G1) is described. The monoanionic ligand L is preferably any one of a monoanionic bidentate chelate ligand having a β-diketone structure, a monoanionic bidentate chelate ligand having a carboxyl group, a monoanionic bidentate chelate ligand having a phenolic hydroxyl group, or a monoanionic bidentate chelate ligand in which both two ligand elements are nitrogen, because these ligands have high coordinating ability. Specific examples of the monoanionic ligand L include, but not limited to, the monoanionic ligands represented by the structural formulae (L1) to (L9) below.

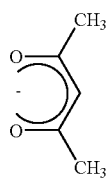

(L1)

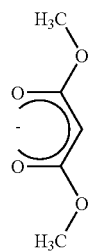

(L2)

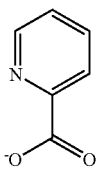

(L3)

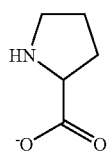

(L4)

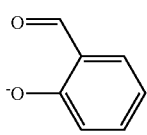

(L5)

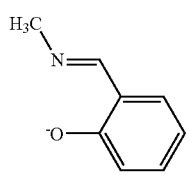

(L6)

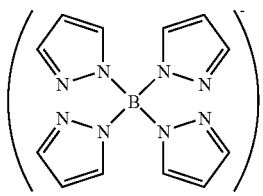

(L7)

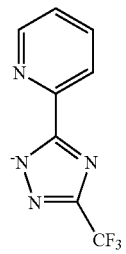

(L8)

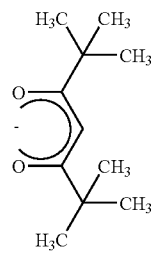

(L9)

By using the above-described central metal M, ligand portion P, and monoanionic ligand L in combination as appropriate, the organometallic complexes of the present invention are formed. Hereinafter, specific structural formulae of the organometallic complexes of the present invention are given (structural formulae (1) to (59) below). Note that the present invention is not limited to these complexes.

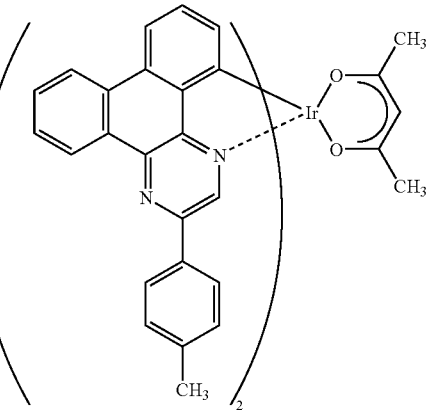

(1)

(2)
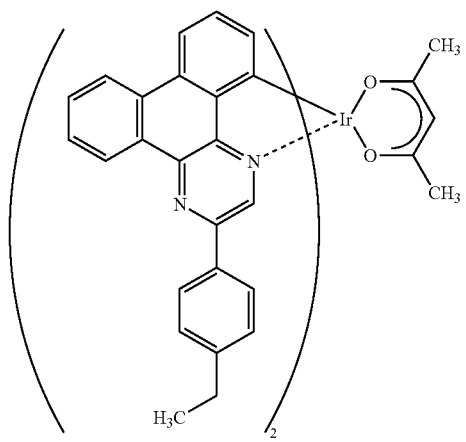
(3)
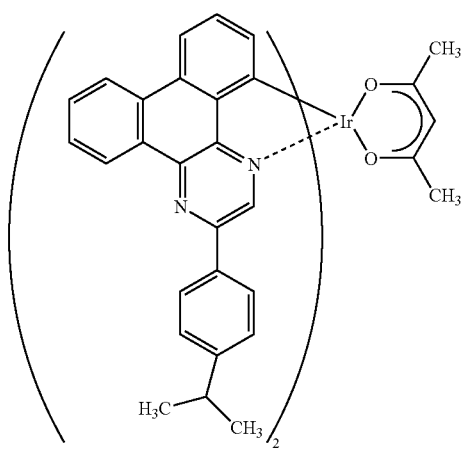
(4)
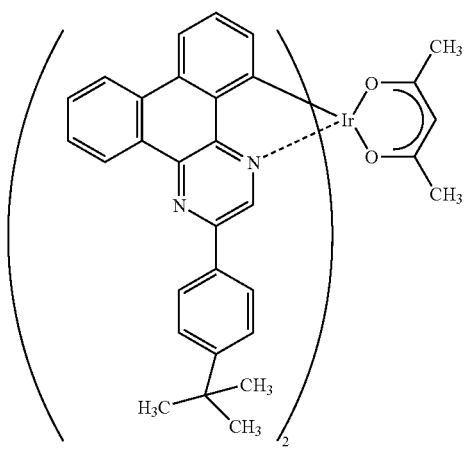
(5)
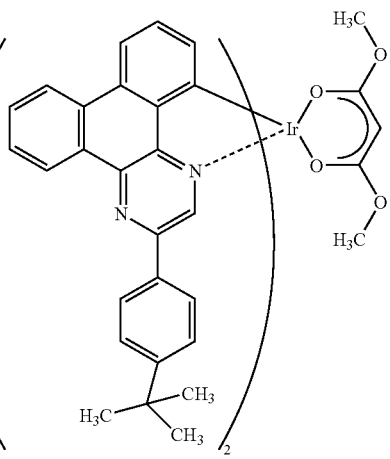
(6)
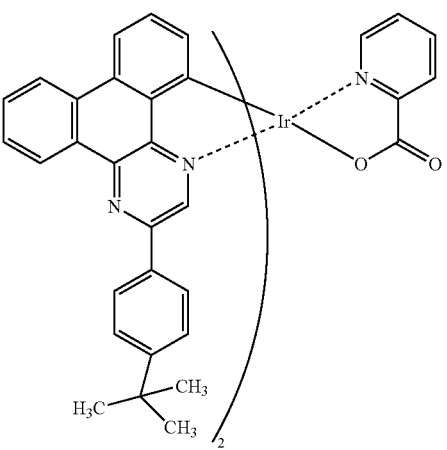
(7)
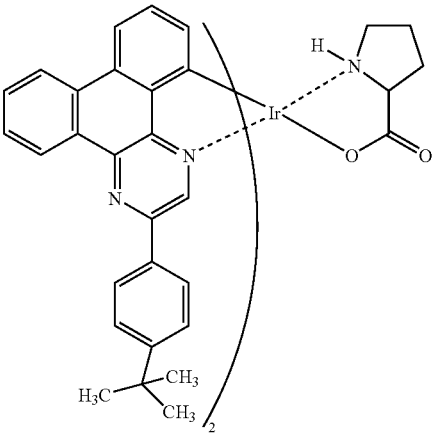

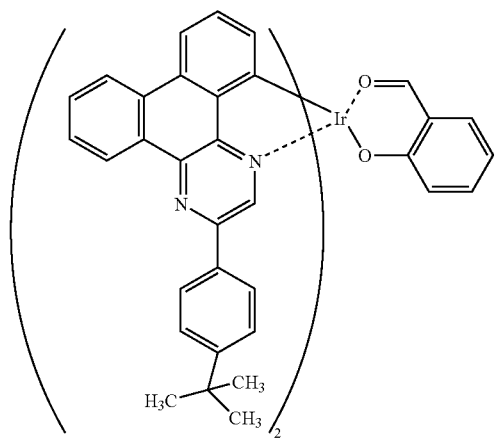
(8)
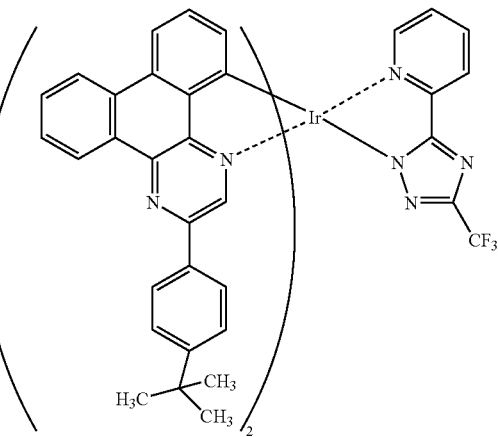
(11)
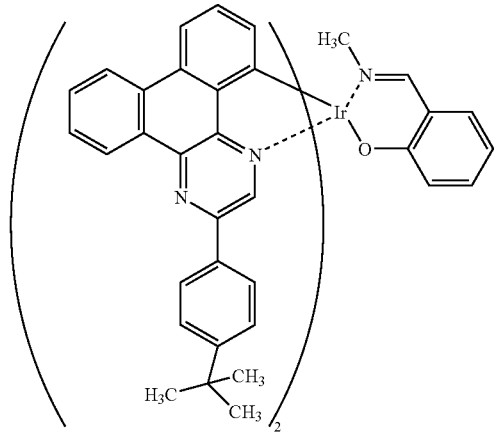
(9)
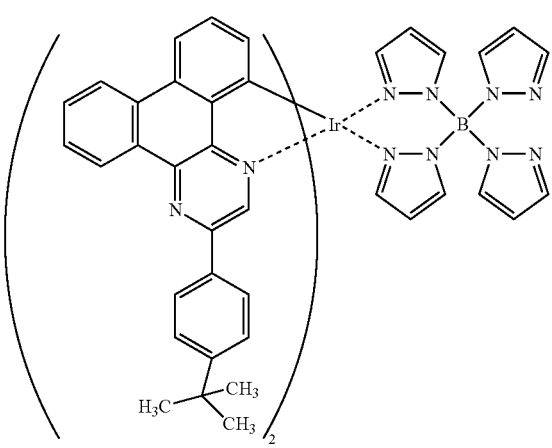
(10)
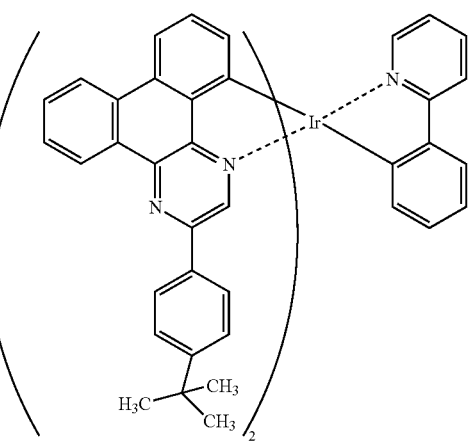
(13)

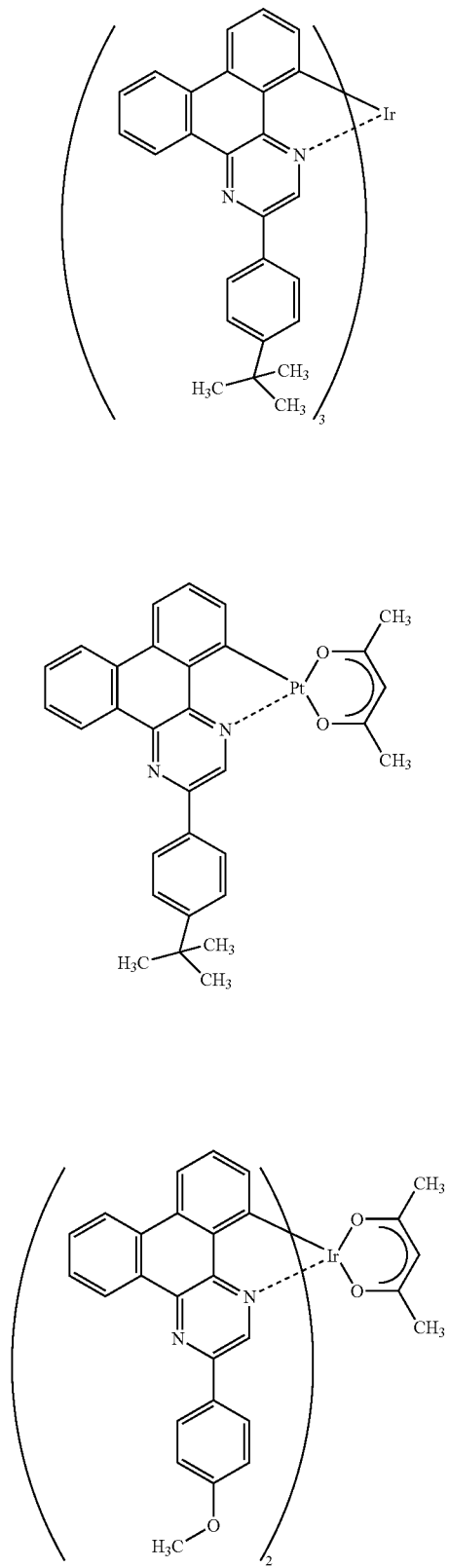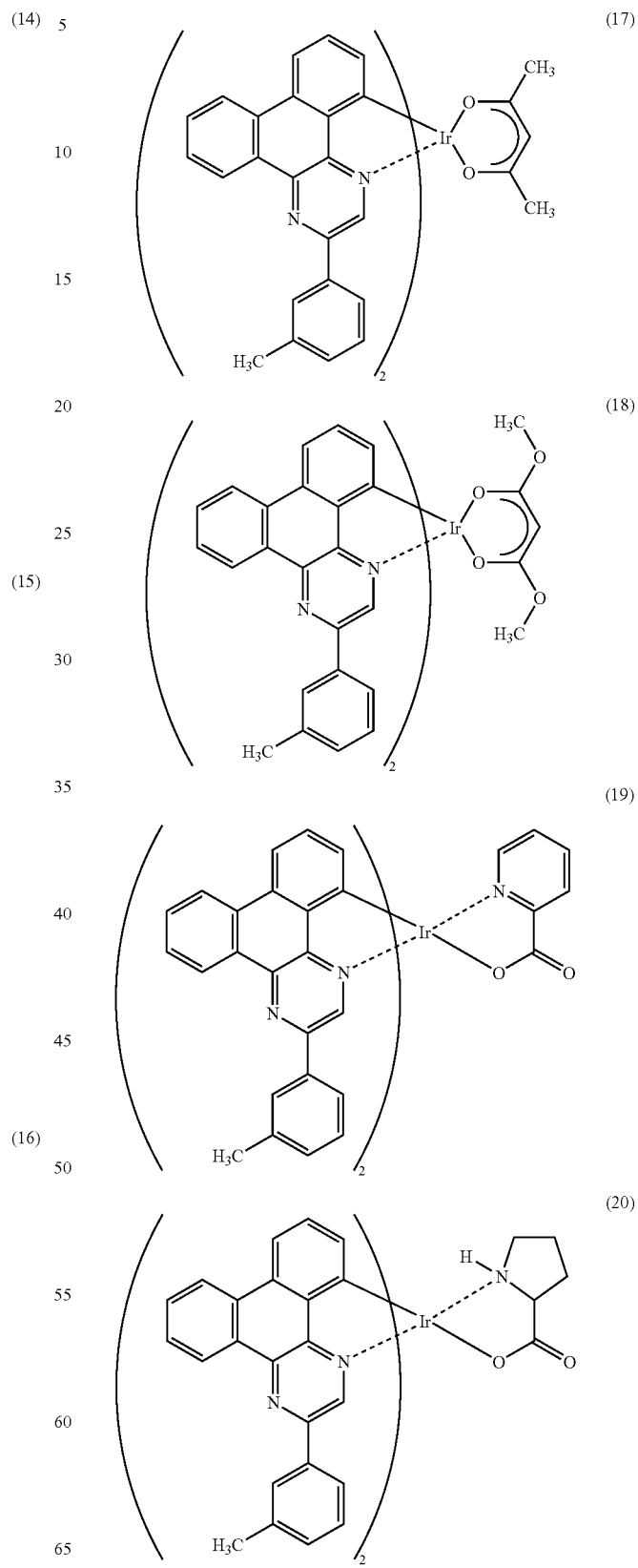

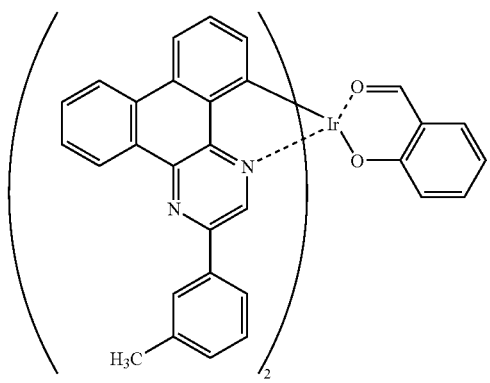
(21)
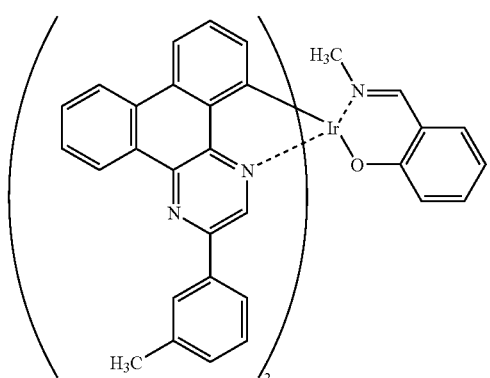
(22)
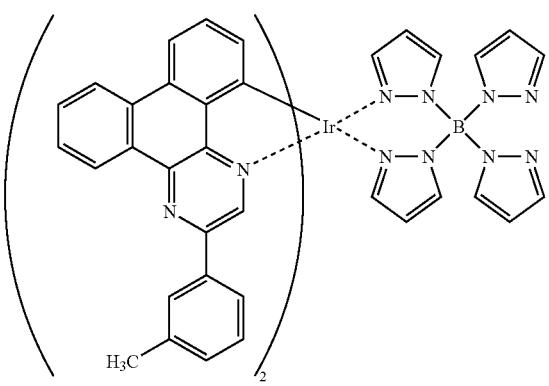
(23)
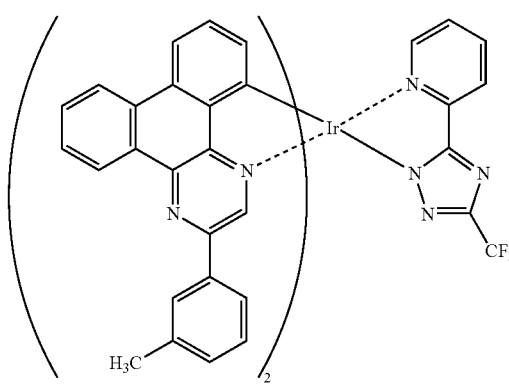
(24)
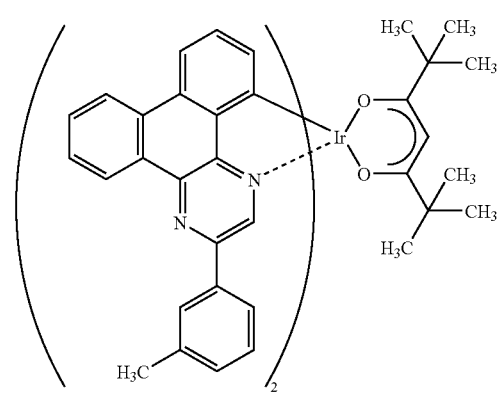
(25)
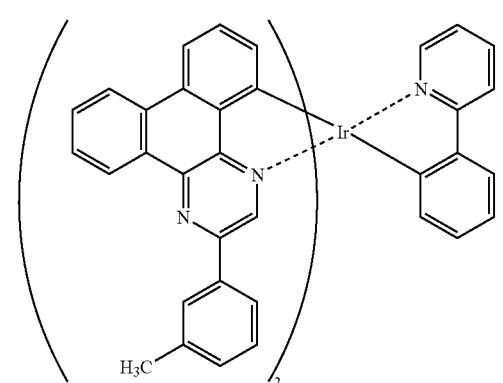
(26)
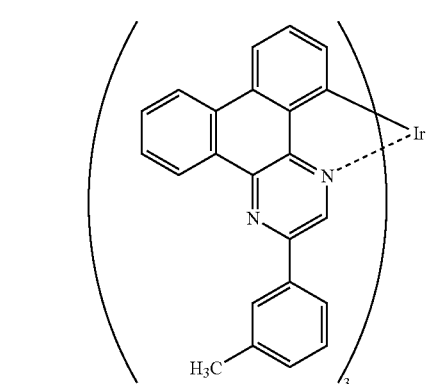
(27)
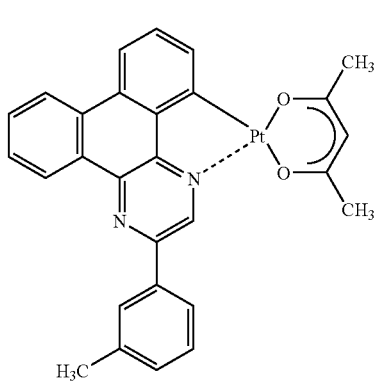
(28)

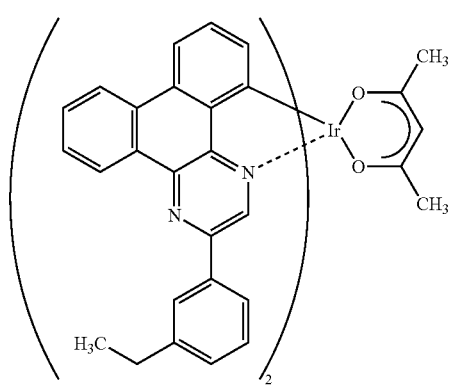
(29)
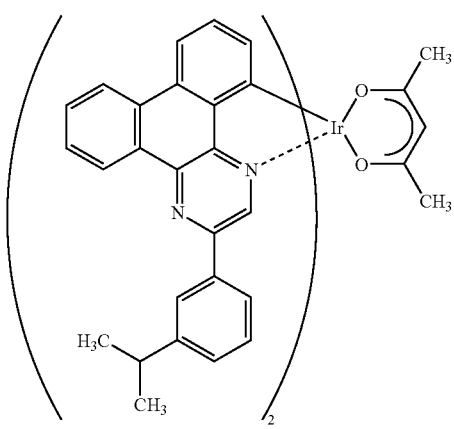
(30)
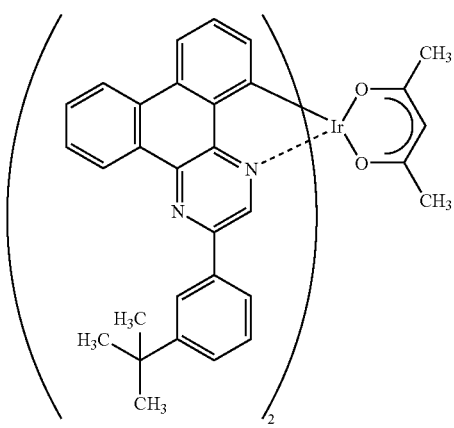
(31)
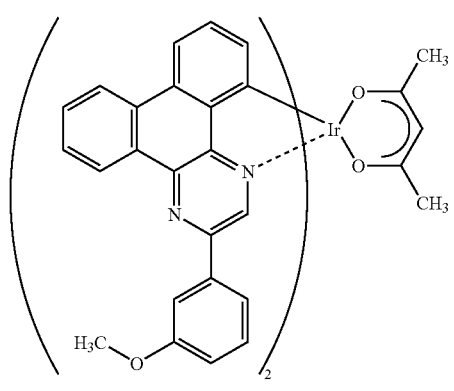
(32)
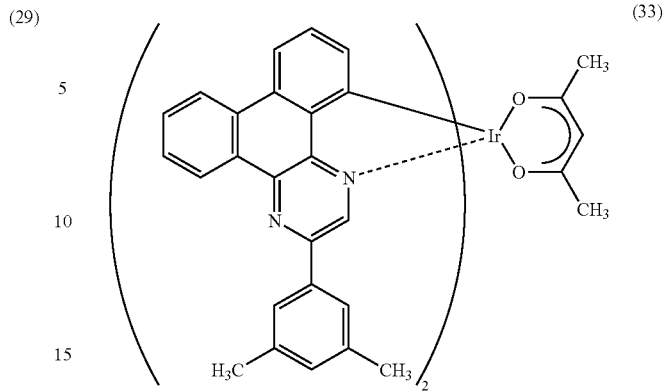
(33)
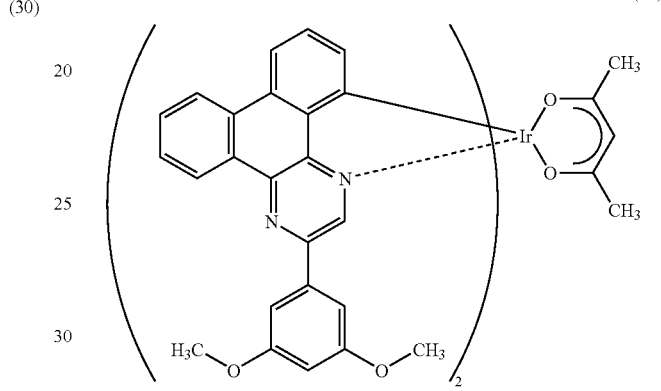
(34)
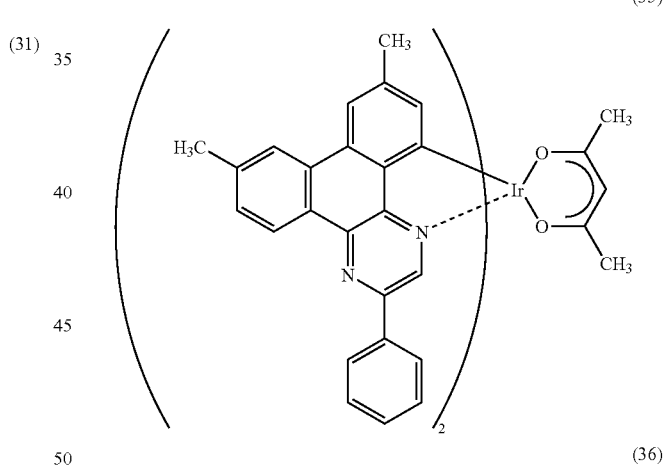
(35)
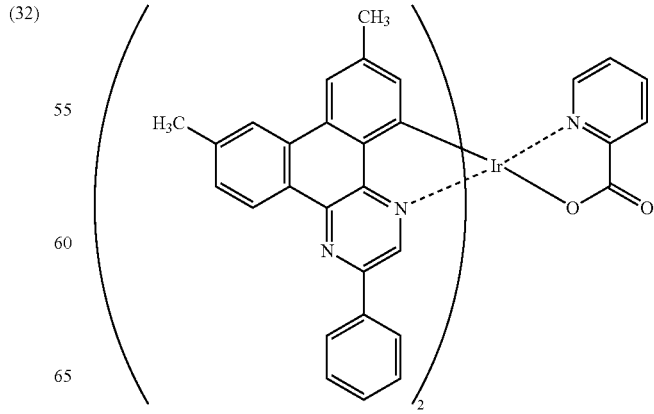
(36)

(37)
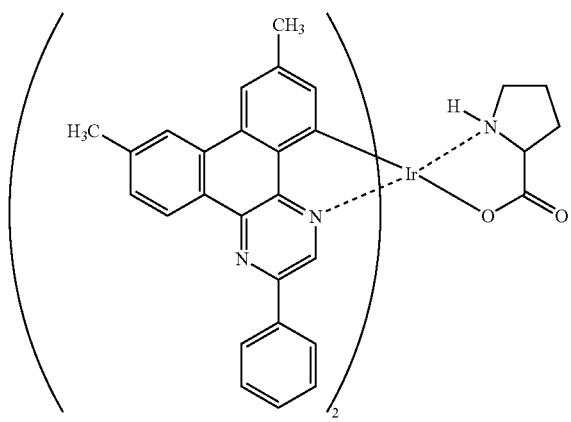
(38)
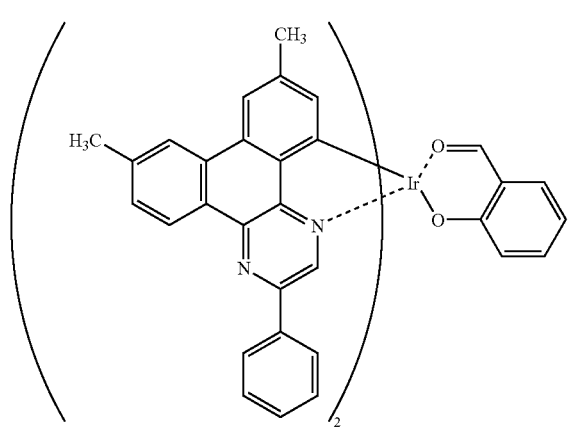
(39)
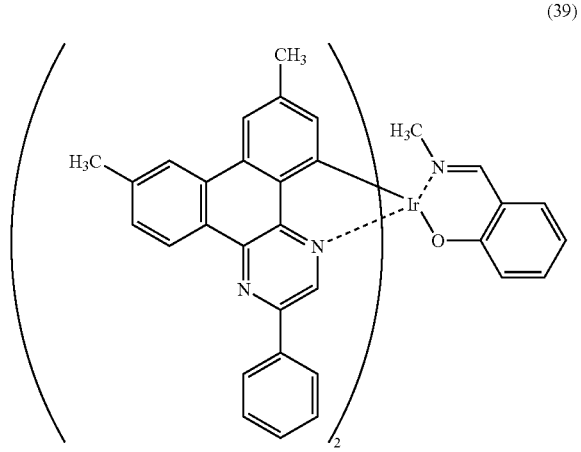
(40)
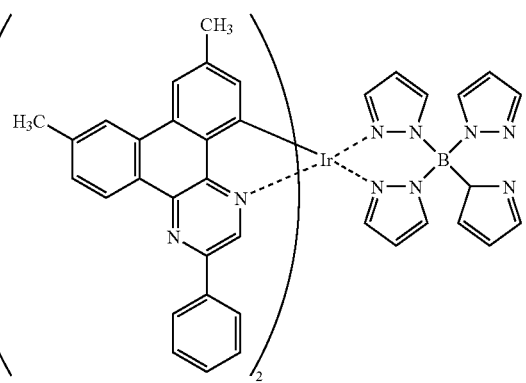
(41)
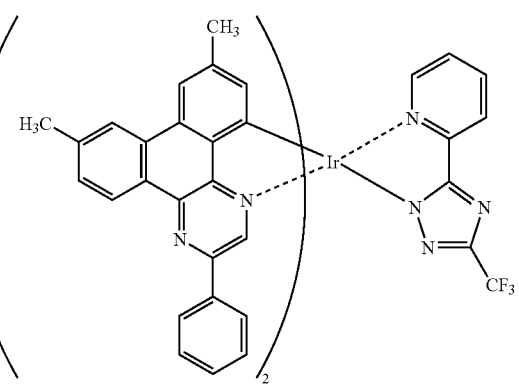
(42)
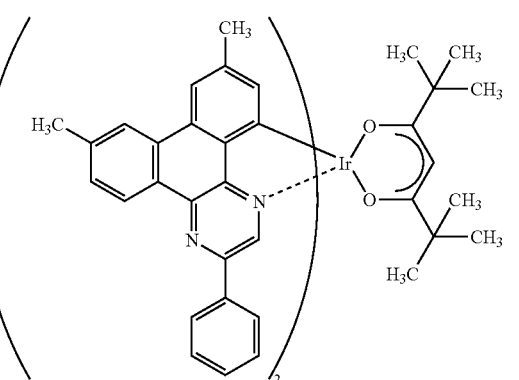
(43)
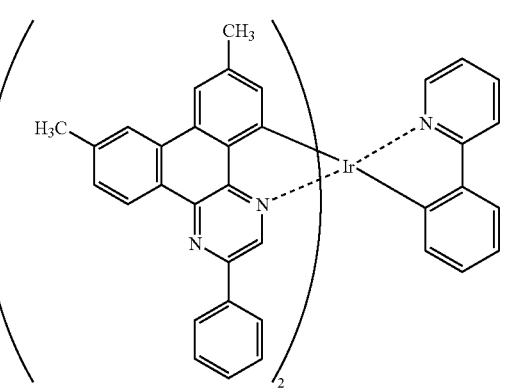

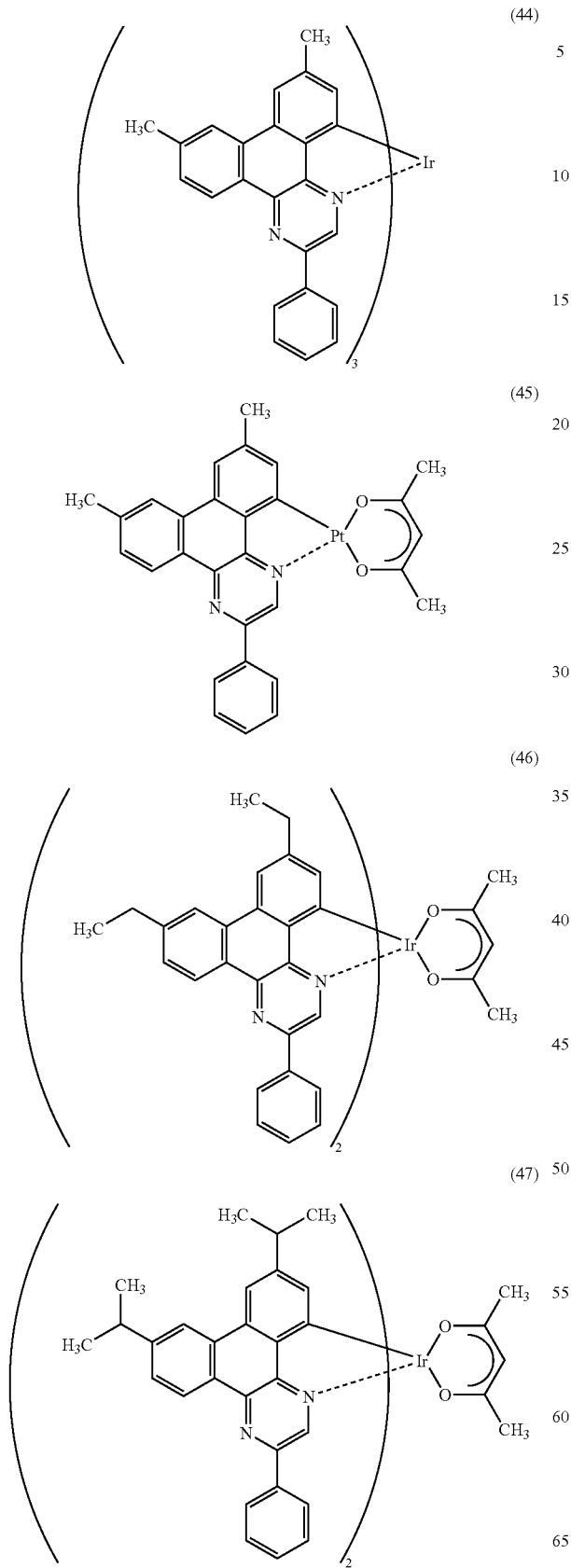
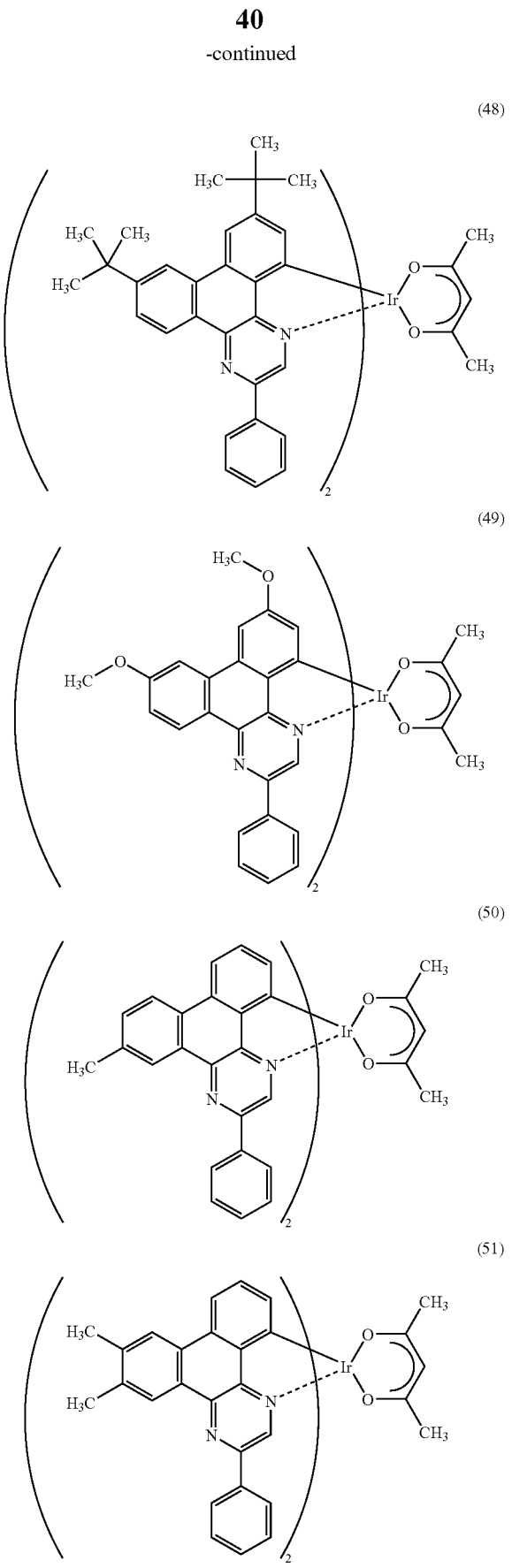

-continued
(52)
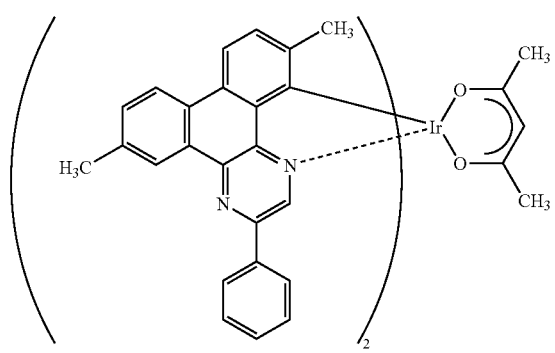
(53)
(56)
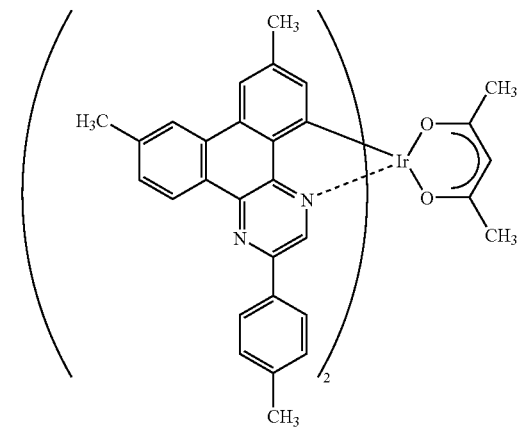
(57)
(54)
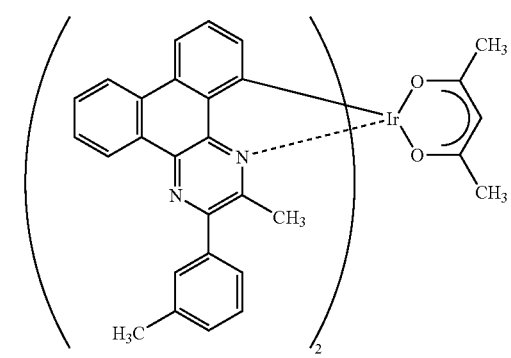
(55)
(58)
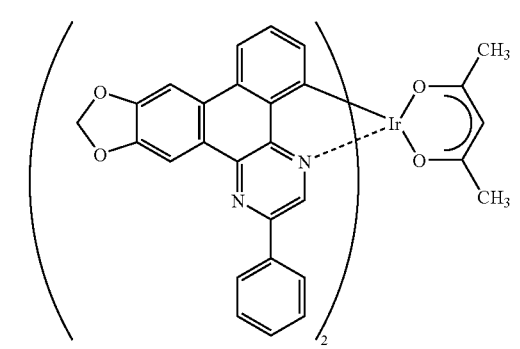
(59)
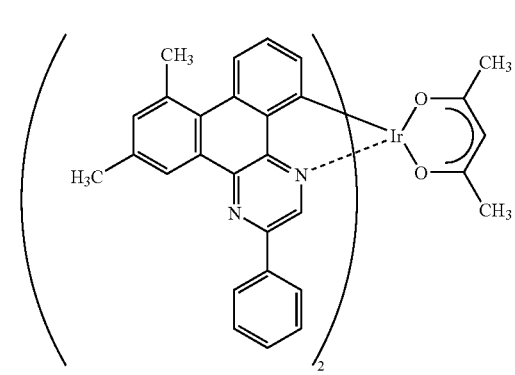
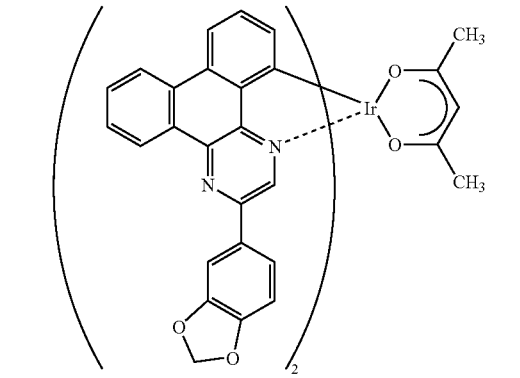

In the organometallic complexes represented by the above structural formulae (1) to (59), there can be a geometrical isomer and a stereoisomer according to the type of ligand. The organometallic complexes of the present invention include all types of such isomers. In addition, as the organometallic complex represented by the structural formula (27) and the organometallic complex represented by the structural formula (44), there are two geometrical isomers of a facial isomer and a meridional isomer. The organometallic complex of the present invention includes both isomers.

The foregoing organometallic complex of the present invention can be used as a photosensitizer owing to capability of intersystem crossing. Further, it can exhibit phosphorescence. Thus, the organometallic complexes of the present invention can each be used as a light-emitting material or a light-emitting substance for a light-emitting element.

Further, a feature of an organometallic complex of the present invention is that purification after the synthesis is easy. The introduced alkyl or alkoxy group renders the compound soluble to facilitate the purification by a recrystallization method or a column chromatography method. Furthermore, the introduced alkyl or alkoxy group decreases cohesion to facilitate purification by a sublimation purification method.

Embodiment 2

In Embodiment 2, an embodiment of a light-emitting element that has any of the organometallic complexes of the present invention which is described in Embodiment 1 as a light-emitting substance will be described using FIG. 1.

FIG. 1 illustrates a light-emitting element that has a light-emitting layer 113 formed between a first electrode 101 and a second electrode 102. Further, the light-emitting layer 113 includes an organometallic complex of the present invention as described above in Embodiment 1.

By applying a voltage to such a light-emitting element, holes injected from the first electrode 101 side and electrons injected from the second electrode 102 side recombine in the light-emitting layer 113 to produce an excited state of the organometallic complex of the present invention. Then, when the organometallic complex returns to a ground state from the excited state, it emits light. The organometallic complex of the present invention thus functions as a light-emitting substance of the light-emitting element. Note that the first electrode 101 and the second electrode 102 function as an anode and a cathode, respectively, in the light-emitting element of Embodiment 2.

Here, the light-emitting layer 113 includes any of the organometallic complexes of the present invention. The light-emitting layer 113 preferably includes a substance having larger triplet excitation energy than that of the organometallic complex of the present invention as a substance used for dispersion of the organometallic complex of the present invention (i.e., as a host), and also includes the dispersed organometallic complex of the present invention as a guest. Accordingly, light emitted from the organometallic complex of the present invention can be prevented from being quenched due to concentration. Note that triplet excited energy means an energy gap between a ground state and a triplet excited state.

Further, any of the organometallic complexes of the present invention may be dispersed in a single host material or in a mixture of a plurality of host materials. For example, the light-emitting layer may include a mixture of any of the organometallic complexes of the present invention, an organic compound having a hole-transport property, and an organic compound having an electron-transport property.

In order to obtain the optimum carrier balance for the light-emitting layer including a dispersed organometallic complex, it is effective to use a material in which an organic compound having a hole-transport property and an organic compound having an electron-transport property are mixed as a host material. Further, since the light-emitting region is expanded, it can be expected that emission efficiency or reliability of the light-emitting element is increased.

Examples of organic compounds having a hole-transport property which can be used for the host material include an aromatic amine compound such as 4,4'-bis[N-(1-naphthyl)-N-phenylamino]biphenyl (abbreviation: NPB), 4,4'-bis[N-(9-phenanthryl)-N-phenylamino]biphenyl (abbreviation: PPB), 4,4'-bis[N-(3-methylphenyl)-N-phenylamino]biphenyl (abbreviation: TPD), 4,4'-bis[N-(9,9-dimethylfluoren-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: m-MTDATA), 4,4',4"-tri(N-carbazolyl)triphenylamine (abbreviation: TCTA), 1,1-bis[4-(diphenylamino)phenyl]cyclohexane (abbreviation: TPAC), 9,9-bis[4-(diphenylamino)phenyl]fluorene (abbreviation: TPAF), 4-(9H-carbazolyl)-4'-(5-phenyl-1,3,4-oxadiazol-2-yl)triphenylamine (abbreviation: YGAO11), or N-[4-(9-carbazolyl)phenyl]-N-phenyl-9,9-dimethylfluoren-2-amine (abbreviation: YGAF) and a carbazole derivative such as 4,4'-di(N-carbazolyl)biphenyl (abbreviation: CBP), 1,3-bis(N-carbazolyl)benzene (abbreviation: mCP) or 1,3,5-tris(N-carbazolyl)benzene (abbreviation: TCzB).

Examples of organic compounds having an electron-transport property which can be used for the host material include a heteroaromatic compound such as 9-[4-(5-phenyl-1,3,4-oxadiazol-2-yl)phenyl]carbazole (abbreviation: CO11), 1,3-bis[5-(p-tert-buthylphenyl)-1,3,4-oxadiazol-2-yl]benzene (abbreviation: OXD-7), 2-(4-biphenylyl)-5-(4-tert-butylphenyl)-1,3,4-oxadiazole (abbreviation: PBD), 2,2',2"-(1,3,5-benzenetriyl)tris(1-phenyl-1H-benzimidazole) (abbreviation: TPBI), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), 9,9',9"-[1,3,5-triazine-2,4,6-triyl]tricarbazole (abbreviation: TCzTRZ), 2,2',2"-(1,3,5-benzenetriyl)tris(6,7-dimethyl-3-phenylquinoxaline) (abbreviation: TriMeQn), 2,3-bis(4-diphenylaminophenyl)quinoxaline (abbreviation: TPAQn), 9,9'-(quinoxaline-2,3-diyldi-4,1-phenylene)di(9H-carbazole) (abbreviation: CzQn), 3,3',6,6'-tetraphenyl-9,9'-(quinoxaline-2,3-diyldi-4,1-phenylene)di(9H-carbazole) (abbreviation: DCzPQ), bathophenanthroline (abbreviation: BPhen), or bathocuproine (abbreviation: BCP), and a metal complex such as tris(8-quinolinolato)aluminum (abbreviation: Almq$_3$), bis(2-methyl-8-quinolinolato)(4-phenylphenolato)aluminum(III) (abbreviation: BAlq), tris[2-(2-hydroxyphenyl)-5-phenyl-1,3,4-oxadiazolato]aluminum(III) (abbreviation: Al(OXD)$_3$), tris(2-hydroxyphenyl-1-phenyl-1H-benzimidazolato)aluminum(III) (abbreviation: Al(BIZ)$_3$), bis[2-(2-hydroxyphenyl)benzothiazolato]zinc(II) (abbreviation: Zn(BTZ)$_2$), bis[2-(2-hydroxyphenyl)benzoxazolato]zinc(II) (abbreviation: Zn(PBO)$_2$), or bis[2-(2-hydroxyphenyl)pyridinato]zinc (abbreviation: Znpp$_2$).

Note that the light-emitting layer 113 can be formed by, for example, a sputtering method, an evaporation method, or the like. Into the organometallic complexes of the present invention, an alkyl or alkoxy group is introduced. Such a substituent which has high volume decreases cohesion and imparts a sublimation property.

Alternatively, the light-emitting layer 113 can be formed in such a manner that application liquid obtained by dissolving or dispersing any of the organometallic complexes of the present invention and the host material in an appropriate solvent is applied by a wet method such as an inkjet method or a spin coating method. Since an alkyl group or alkoxy group is introduced into any of the organometallic complexes of the present invention, each organometallic complex has high affinity with a solvent and therefore can be used in combination with any of a variety of solvents.

As the solvent, a solvent having an aromatic ring (e.g., a benzene ring), such as toluene or methoxybenzene (anisole), can be used. Further, examples of the solvents which can be used include, but not limited to, an organic solvent that does not have aromatic rings, such as dimethylsulfoxide (DMSO), dimethylformamide (DMF), or chloroform, an ether such as diethyl ether, dioxane, or tetrahydrofuran (THF), an alcohol such as methanol, ethanol, isopropanol, butanol, 2-methoxyethanol, or 2-ethoxyethanol, acetonitrile, a mixed solvent thereof, and the like.

In the case of forming a stack of organic thin films by a wet method, since materials from which the films are formed are dissolved, a solvent in which the underlying film is insoluble is needed to prepare the application liquid. Because of the solubility of the organometallic complexes of the present invention, the solvent is readily selected.

In addition, the solvent is preferably a volatile organic solvent having a boiling point of from 50 to 200° C. so as not to remain in the films.

When a stack of organic thin films are formed by a wet method, the substance used for dispersion of any of the organometallic complexes of the present invention (i.e., host) can be selected from the above-described organic compounds having a hole-transport property and organic compounds having an electron-transport property and also from high molecular compounds having a hole-transport property and high molecular compounds having an electron-transport property.

Furthermore, in order to improve properties of the film formed, a binder may be contained. For the binder, use of a high molecular compound that is electrically inactive is preferable. Specifically, polymethylmethacrylate (abbreviation: PMMA), polyimide, or the like can be used.

Further, any of the organometallic complexes of the present invention may be dispersed in a single host material or in a mixture of a plurality of host materials. For example, the light-emitting layer may include a mixture of any of the organometallic complexes of the present invention, an organic compound having a hole-transport property, and an organic compound having an electron-transport property.

Examples of high molecular compounds having a hole-transport property which can be used for the host material include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), poly[N,N'-bis(4-butylphenyl)-N,N'-bis(phenyl)benzidine (abbreviation: Poly-TPD), and the like.

Examples of high molecular compounds having an electron-transport property which can be used for the host material include poly(2,5-pyridinediyl) (abbreviation: PPy), poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy), and the like.

Note that the organometallic complexes of the present invention emit red light with high color purity and has high emission efficiency. Accordingly, by fabrication of a light-emitting element using any of the organometallic complexes of the present invention, it is possible to provide the light-emitting element that can exhibit red light with high color purity, has high emission efficiency, can be driven for a long time, and exhibit red light with high luminous efficiency. In addition, since the light-emitting element of the present invention has high emission efficiency, power consumption can be reduced.

Further, although there is no particular limitation on the first electrode 101, it is preferably formed using a substance having a high work function to enable it to serve as an anode, as in Embodiment 2. Specifically, it is possible to use indium tin oxide (ITO), indium tin oxide containing silicon oxide (ITSO), indium oxide containing zinc oxide at 2 to 20 wt % (IZO), gold (Au), platinum (Pt), nickel (Ni), tungsten (W), chromium (Cr), molybdenum (Mo), iron (Fe), cobalt (Co), copper (Cu), palladium (Pd), or the like. Note that the first electrode 101 can be formed, for example, by a sputtering method, an evaporation method, or the like.

Furthermore, although there is no particular limitation on the second electrode 102, it is preferably formed using a substance having a low work function to enable it to serve as a cathode, as in Embodiment 2. Specifically, it is possible to use aluminum (Al), indium (In), an alkali metal such as lithium (Li) or cesium (Cs), an alkaline-earth metal such as magnesium (Mg) or calcium (Ca), a rare-earth metal such as erbium (Er) or ytterbium (Yb), or the like. Alternatively, an alloy such as aluminum-lithium alloy (AlLi) or magnesium-silver alloy (MgAg) can be used. Note that the second electrode 102 can be formed by, for example, a sputtering method, an evaporation method, or the like.

Note that in order to extract emitted light to the outside, it is necessary that one or both of the first electrode 101 and the second electrode 102 be an electrode formed using a conductive film that can transmit visible light, such as ITO, or an electrode with a thickness of several to several tens of nanometers so as to transmit visible light.

In addition, as illustrated in FIG. 1, a hole-transport layer 112 may be provided between the first electrode 101 and the light-emitting layer 113. Here, the term hole-transport layer means a layer which has the function of transporting holes injected from the first electrode 101 to the light-emitting layer 113. By thus providing the hole-transport layer 112 to separate the first electrode 101 from the light-emitting layer 113, quenching of emitted light due to metal can be prevented. However, the hole-transport layer 112 is not necessarily provided.

Although there is no particular limitation on a substance forming the hole-transport layer 112, any of the following substances can be typically used as this substance: an aromatic amine compound such as 4,4'-bis[N-(1-naphthyl)-N-phenylamino]biphenyl (abbreviation: NPB), 4,4'-bis[N-(3-methylphenyl)-N-phenylamino]biphenyl (abbreviation: TPD), 4,4'-bis[N-(9,9-dimethylfluoren-2-yl)-N-phenylamino]biphenyl (abbreviation: DFLDPBi), 4,4',4''-tris(N,N-diphenylamino)triphenylamine (abbreviation: TDATA), or 4,4',4''-tris[N-(3-methylphenyl)-N-phenylamino]triphenylamine (abbreviation: m-MTDATA), and a high molecular compound such as poly(4-vinyl triphenylamine) (abbreviation: PVTPA).

Note that the hole-transport layer 112 may have a multilayer structure in which two or more layers are stacked. In addition, the hole-transport layer 112 may also be formed by mixing two or more types of substances.

Further, as illustrated in FIG. 1, an electron-transport layer 114 may be provided between the second electrode 102 and the light-emitting layer 113. Here, the term electron-transport layer means a layer having the function of transporting electrons injected from the second electrode 102 to the light-emitting layer 113. By thus providing the electron-transport layer 114 is provided to separate the second electrode 102 from the light-emitting layer 113, quenching of emitted light due to metal can be prevented. Note that the electron-transport layer 114 is not necessarily provided.

Although there is no particular limitation on a substance forming the electron-transport layer 114, the following substances can be typically used as this substance: a metal complex such as tris(8-quinolinolato)aluminum (abbreviation: $Alq_3$), tris(4-methyl-8-quinolinolato)aluminum (abbreviation: $Almq_3$), bis(10-hydroxybenzo[h]quinolinato)beryllium (abbreviation: $BeBq_2$), bis(2-methyl-8-quinolinolato)(4-phenylphenolato)aluminum (abbreviation: BAlq), bis[2-(2-hydroxyphenyl)benzoxazolato]zinc (abbreviation: ZnBOX), or bis[2-(2-hydroxyphenyl)benzothiazolato]zinc (abbreviation: $Zn(BTZ)_2$), a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs), and a high molecular compound such as poly(2,5-pyridine-diyl) (abbreviation: PPy). Note that the electron-transport layer 114 may have a multilayer structure in which two or more layers are stacked. In addition, the electron-transport layer 114 may also be formed by mixing two or more types of substances.

Further, as illustrated in FIG. 1, a hole-inject layer 111 may be provided between the first electrode 101 and the hole-transport layer 112. Here, the term hole-inject layer means a layer that has the function of assisting injection of holes from an electrode functioning as an anode to the hole-transport layer 112. Note that the hole-inject layer 111 is not necessarily provided.

Although there is no particular limitation on a substance forming the hole-inject layer 111, the following substances can be used as this substance: metal oxide such as vanadium oxide, niobium oxide, tantalum oxide, chromium oxide, molybdenum oxide, tungsten oxide, manganese oxide, rhenium oxide, and ruthenium oxide, a phthalocyanine compound such as phthalocyanine (abbreviation: $H_2Pc$), copper phthalocyanine (abbreviation: CuPc), and the like. Alternatively, any of the substances for forming the hole-transport layer 112 as described above can also be used. Further alternatively, a high molecular compound such as a mixture of poly(ethylenedioxythiophene) and poly(styrene sulfonate) (abbreviation: (abbreviation: PEDOT/PSS)) can be used.

Still alternatively, for the hole-inject layer 111, a composite material formed by combining an organic compound and an electron acceptor may be used. Such a composite material is superior in a hole-inject property and a hole-transport property, since holes are generated in the organic compound by the electron acceptor. In this case, the organic compound is preferably a material excellent in transporting the generated holes. Specifically, the foregoing substances for forming the hole-transport layer 112 (e.g., an aromatic amine-based compound) can be used for example. As the electron acceptor, a substance having an electron accepting property to the organic compound may be used. Specifically, transition metal oxide is preferable and examples thereof include vanadium oxide, niobium oxide, tantalum oxide, chromium oxide, molybdenum oxide, tungsten oxide, manganese oxide, rhenium oxide, ruthenium oxide, and the like. Lewis acid such as iron chloride(III) or aluminum chloride(III) can also be used. Alternatively, an organic compound such as 7,7,8,8-tetracyano-2,3,5,6-tetrafluoroquinodimethane (abbreviation: $F_4$-TCNQ) can also be used. Note that the hole-inject layer 111 may have a multilayer structure in which two or more layers are stacked. In addition, the hole-inject layer 111 may also be formed by mixing two or more types of substances.

Further, as illustrated in FIG. 1, an electron-inject layer 115 may be provided between the second electrode 102 and the electron-transport layer 114. Here, the term electron-inject layer means a layer which has the function of assisting injection of electrons from the electrode functioning as a cathode to the electron-transport layer 114. Note that the electron-inject layer 115 is not necessarily provided.

Although there is no particular limitation on a substance forming the electron-inject layer 115, the following substances can be used as this substance: an alkali metal compound or an alkaline-earth metal compound such as lithium fluoride (LiF), cesium fluoride (CsF), calcium fluoride ($CaF_2$), or lithium oxide and a rare earth metal compound such as erbium fluoride ($ErF_3$). Alternatively, the above-mentioned substances for forming the electron-transport layer 114 can also be used.

Alternatively, for the electron-inject layer 115, a composite material formed by combining an organic compound and an electron donor may be used. The composite material is superior in an electron-inject property and an electron-transport property, since electrons are generated in the organic compound by the electron donor. In this case, the organic compound is preferably a material excellent in transporting the generated electrons. Specifically, the foregoing materials for forming the electron-transport layer 114 (e.g., a metal complex or a heteroaromatic compound) can be used for example. As the electron donor, a substance exhibiting an electron donating property to the organic compound may be used, and there are an alkali metal, an alkaline-earth metal or a rare earth metal, for example, lithium, cesium, magnesium, calcium, erbium, and ytterbium. Further, an alkali metal oxide or an alkaline-earth metal oxide is preferable, and there are, for example, lithium oxide, calcium oxide, barium oxide, and the like. Alternatively, Lewis acid such as magnesium oxide can also be used. Further alternatively, an organic compound such as tetrathiafulvalene (abbreviation: TTF) can be used.

In the foregoing light-emitting element of the present invention, each of the hole-inject layer 111, the hole-transport layer 112, the light-emitting layer 113, the electron-transport layer 114, and the electron-inject layer 115 may be formed by any method, for example, an evaporation method, an inkjet method, an application method, or the like. In addition, each of the first electrode 101 and the second electrode 102 may also be formed by any of a sputtering method, an evaporation method, or the like, or a wet method such as an inkjet method or a coating method.

Embodiment 3

The light-emitting element according to the present invention may have a plurality of light-emitting layers. For example, by providing a plurality of light-emitting layers and mixing light emitted from the light-emitting layers, emitted light which is a combination of the light emitted from the plurality of layers can be obtained. Thus, white light emission can be obtained, for example. In Embodiment 3, an embodiment of a light-emitting element having a plurality of light-emitting layers is described with reference to FIG. 2.

Figure 2:
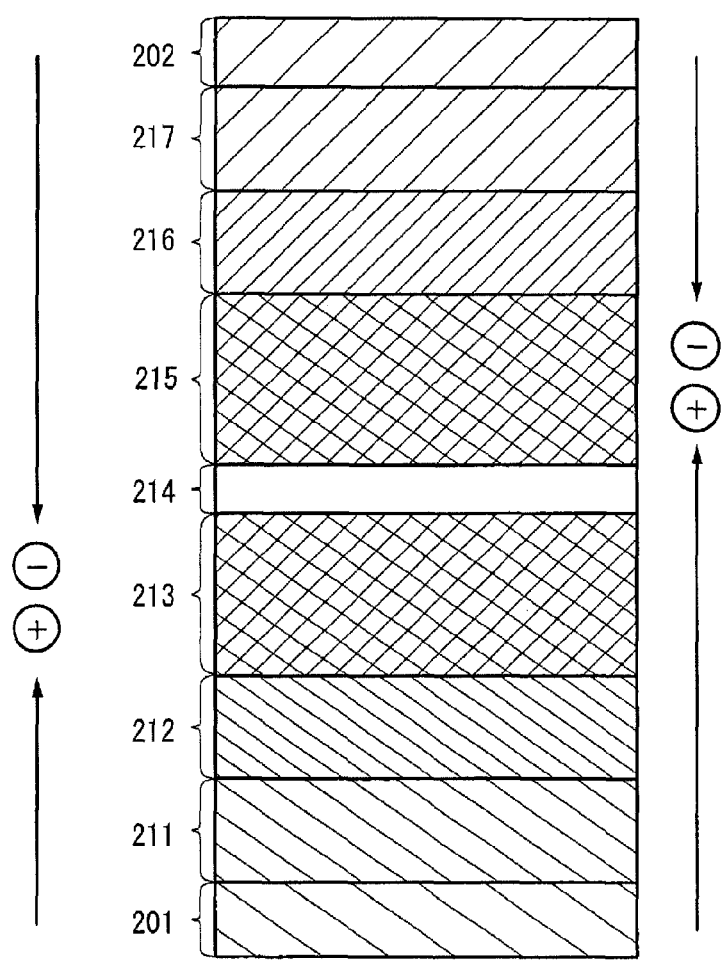
FIG. 2 illustrates a light-emitting element according to an embodiment of the present invention.

In FIG. 2, a first light-emitting layer 213 and a second light-emitting layer 215 are provided between a first electrode 201 and a second electrode 202. Light which is a combination of light emitted from the first light-emitting layer 213 and light emitted from the second light-emitting layer 215 can be obtained. A separation layer 214 is preferably formed between the first light-emitting layer 213 and the second light-emitting layer 215.

When a voltage is applied so that the potential of the first electrode 201 is higher than the potential of the second electrode 202, a current flows between the first electrode 201 and the second electrode 202, and holes and electrons recombine in the first light-emitting layer 213, the second light-emitting layer 215, or the separation layer 214. Generated excitation energy is distributed to the first light-emitting layer 213 and the second light-emitting layer 215 to produce an excited state of each of a first light-emitting substance included in the first light-emitting layer 213 and a second light-emitting substance included in the second light-emitting layer 215. The excited first and second light-emitting substances emit light while returning to the ground states.

The first light-emitting layer 213 includes the first light-emitting substance typified by a fluorescent compound such as perylene, 2,5,8,11-tetra(tert-butyl)perylene (abbreviation: TBP), 4,4'-bis(2,2-diphenylvinyl)biphenyl (abbreviation: DPVBi), 4,4'-bis[2-(9-ethylcarbazol-3-yl)vinyl]biphenyl (abbreviation: BCzVBi), bis(2-methyl-8-quinolinolato)(4-phenylphenolato)aluminum (abbreviation: BAlq), or bis(2-methyl-8-quinolinolato)galliumchloride (abbreviation: $Gamq_2Cl$); or a phosphorescent compound such as bis{2-[3',5'-bis(trifluoromethyl)phenyl]pyridinato-$N,C^{2'}$}iridium(III) picolinate (abbreviation: $Ir(CF_3\ ppy)_2(pic)$), bis[2-(4',6'-difluorophenyl)pyridinato-$N,C^{2'}$]iridium(III) acetylacetonate (abbreviation: FIr(acac)), bis[2-(4',6'-difluorophenyl)pyridinato-$N,C^{2'}$]iridium(III)picolinate (abbreviation: FIrpic), or bis[2-(4',6'-difluorophenyl)pyridinato-$N,C^{2'}$]iridium(III) tetra(1-pyrazolyl)borate (abbreviation: $FIr_6$), from which light emission with a peak at 450 to 510 nm in an emission spectrum (i.e., blue light to blue green light) can be obtained. In addition, when the first light-emitting substance is a fluorescent compound, preferably, the light-emitting layer 213 has a structure in which a substance having larger singlet excited energy than that of the first light-emitting substance is used as a first host and the dispersed first light-emitting substance is included as a guest. Alternatively, when the first light-emitting substance is a phosphorescent compound, preferably, the light-emitting layer 213 has a structure in which a substance having larger triplet excited energy than that of the first light-emitting substance is used as the first host and the dispersed first light-emitting substance is included as the guest. As the first host, NPB, CBP, TCTA, or the like which is described above, 9,10-di(2-naphthyl)anthracene (abbreviation: DNA), 2-tert-butyl-9,10-di(2-naphthyl)anthracene (abbreviation: t-BuDNA) or the like can be used. Note that the singlet excitation energy is an energy difference between a ground state and a singlet excited state. In addition, the triplet excitation energy is an energy difference between a ground state and a triplet excited state.

On the other hand, the second light-emitting layer 215 includes any of the organometallic complexes of the present invention and can emit red light. Further, since any of the organometallic complexes of the present invention has high emission efficiency, a light-emitting element with high emission efficiency can be obtained. Further, a light-emitting element that can be driven for a long time and has reduced power consumption can be obtained.

The second light-emitting layer 215 may have a structure similar to that of the light-emitting layer 113 described above in Embodiment 2.

In addition, the separation layer 214 can be formed using TPAQn, NPB, CBP, TCTA, $Znpp_2$, ZnBOX or the like described above, specifically. By thus providing the separation layer 214, a defect that emission intensity of one of the first light-emitting layer 213 and the second light-emitting layer 215 is stronger than that of the other can be prevented. Note that the separation layer 214 is not necessarily provided, and it may be provided as appropriate such that the ratio of emission intensity between the first light-emitting layer 213 and the second light-emitting layer 215 can be adjusted.

Note that in Embodiment 3, any of the organometallic complexes of the present invention is used for the second light-emitting layer 215, and another light-emitting substance is used for the first light-emitting layer 213; however, any of the organometallic complexes of the present invention may be used for the first light-emitting layer 213, and another light-emitting substance may be used for the second light-emitting layer 215.

Further, in Embodiment 3, a light-emitting element including two light-emitting layers is described as illustrated in FIG. 2; however, the number of the light-emitting layers is not limited to two, and may be three, for example. In addition, light emission from each light-emitting layer may be mixed. As a result, white light emission can be obtained, for example.

Note that the first electrode 201 may have a structure similar to that of the first electrode 101 described above in Embodiment 2. Further, the second electrode 202 may also have a structure similar to that of the second electrode 102 described above in Embodiment 2.

Further, in Embodiment 3, as illustrated in FIG. 2, a hole-inject layer 211, a hole-transport layer 212, an electron-transport layer 216, and an electron-inject layer 217 are provided. As to structures of these layers, the structures of the respective layers described in Embodiment 2 may be applied. However, these layers are not necessarily provided and may be provided according to element characteristics.

Embodiment 4

In Embodiment 4, a light-emitting element in which a plurality of light-emitting layers are provided and light is emitted from these layers with a different element structure from that in Embodiment 3 will be exemplified. Accordingly, also in Embodiment Mode 4, light which is a combination of light emitted from the plurality of layers can be obtained. In other words, white light can be obtained. Hereinafter, description is made using FIG. 3.

Figure 3:
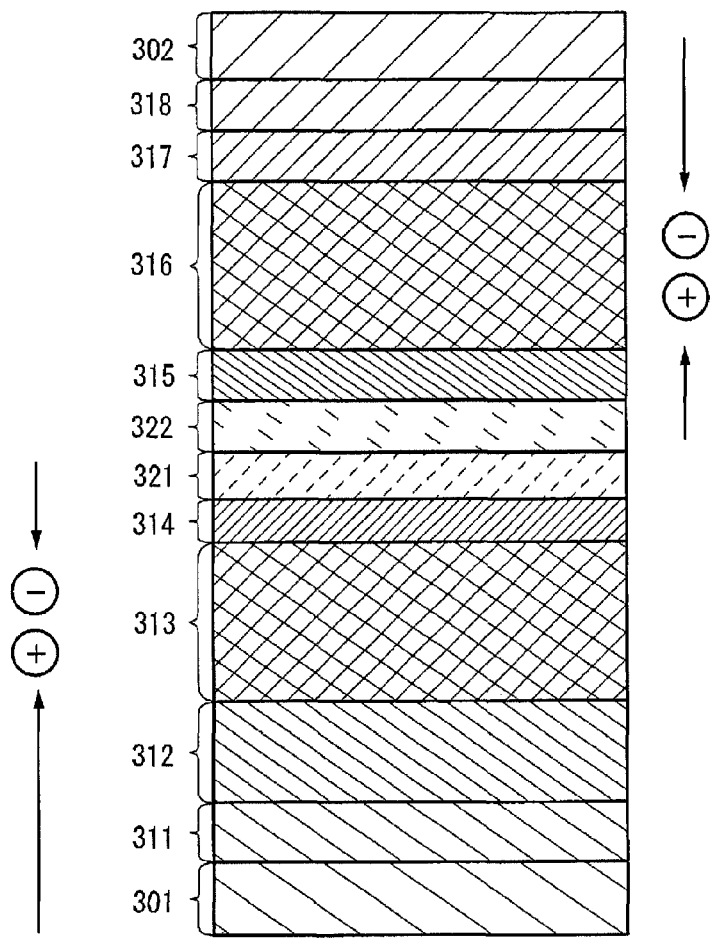
FIG. 3 illustrates a light-emitting element according to an embodiment of the present invention.

In the light-emitting element of FIG. 3, a first light-emitting layer 313 and a second light-emitting layer 316 are provided between a first electrode 301 and a second electrode 302. An N layer 321 and a P layer 322 are provided as charge generating layers between the first light-emitting layer 313 and the second light-emitting layer 316.

The N layer 321 is a layer that generates electrons, and the P layer 322 is a layer that generates holes. When a voltage is applied such that the potential of the first electrode 301 is higher than that of the second electrode 302, holes injected from the first electrode 301 and electrons injected from the N layer 321 recombine in the first light-emitting layer 313, and thus a first light-emitting substance included in the first light-emitting layer 313 emits light. Further, electrons injected from the second electrode 302 and holes injected from the P layer 322 recombine in the second light-emitting layer 316, and thus a second light-emitting substance included in the second light-emitting layer 316 emits light.

The first light-emitting layer 313 may have a structure similar to that of the first light-emitting layer 213 of Embodiment 3, and light with a peak of emission spectrum at 450 to 510 nm (i.e., blue light to blue green light) can be obtained. The second light-emitting layer 316 may have a structure similar to that of the second light-emitting layer 215 of Embodiment 3, and includes any of the organometallic complexes of the present invention to exhibit red light emission. Since any of the organometallic complexes of the present invention has high emission efficiency, a light-emitting element with high emission efficiency and reduced power consumption can be obtained.

Since the N layer 321 is a layer that generates electrons, it may be formed using the composite material formed by combining the organic compound and the electron donor which is described above in Embodiment 2. By adopting such a structure, electrons can be injected to the first light-emitting 313 side.

Since the P layer 322 is a layer that generates holes, it may be formed using the composite material formed by combining the organic compound and the electron acceptor which is described above in Embodiment 2. With such a structure, holes can be injected to the second light-emitting layer 316 side. Further, for the P layer 322, metal oxide having an excellent hole-inject property, such as molybdenum oxide, vanadium oxide, ITO, or ITSO, can be used.

Further, Embodiment 4 describes a light-emitting element in which the two light-emitting layers are provided as illustrated in FIG. 3; however, the number of light-emitting layers is not limited to two, and may be three, for example. Light emission from each light-emitting layer may be combined. As a result, white light emission can be obtained, for example.

Note that the first electrode 301 may have a structure similar to that of the first electrode 101 described above in Embodiment 2. The second electrode 302 may also have a structure similar to that of the second electrode 102 described above in Embodiment 2.

Further, in Embodiment 4, as illustrated in FIG. 3, a hole-inject layer 311, hole-transport layers 312 and 315, electron-transport layers 314 and 317, and an electron-inject layer 318 are provided. As to structures of these layers, the structures of their respective layers described above in Embodiment 2 may also be applied. However, these layers are not necessarily provided and may be provided according to element characteristics.

Embodiment 5

In Embodiment 5, an embodiment of a light-emitting element using any the organometallic complexes of the present invention as a sensitizer will be described with reference to FIG. 1.

FIG. 1 illustrates the light-emitting element having the light-emitting layer 113 between the first electrode 101 and the second electrode 102. The light-emitting layer 113 includes any of the organometallic complexes of the present invention as described in Embodiment 1, and a fluorescent compound that can emit light at a longer wavelength than the organometallic complex of the present invention.

In the light-emitting element like this, holes injected from the first electrode 101 and electrons injected from the second electrode 102 recombine in the light-emitting layer 113 to produce an excited state of the fluorescent compound. Then, the excited fluorescent compound emits light while returning to the ground state. At this time, the organometallic complex of the present invention acts as a sensitizer for the fluorescent compound to increase molecules in the singlet excited state of the fluorescent compound. As noted above, by using any of the organometallic complexes of the present invention as a sensitizer, a light-emitting element with good emission efficiency can be obtained. Note that in the light-emitting element in Embodiment 5, the first electrode 101 functions as an anode and the second electrode 102 functions as a cathode.

The light-emitting layer 113 includes any of the organometallic complexes of the present invention, and a fluorescent compound which can emit light at a longer wavelength than the organometallic complex of the present invention. The light-emitting layer 113 may have a structure in which a substance having larger singlet excited energy than that of the fluorescent substance as well as larger triplet excited energy than that of the organometallic complex of the present invention is used as a host, and the organometallic complex of the present invention and the fluorescent compound which are dispersed are included as guests.

There is no particular limitation on the substance used for dispersion of any of the organometallic complexes of the present invention and the fluorescent compound (i.e., host), and the substances given above as examples of the host in Embodiment 2, or the like can be used.

In addition, there is no particular limitation on the fluorescent compound; however, a compound which can exhibit emission of red light to infrared light is preferable, for example, 4-dicyanomethylene-2-isopropyl-6-[2-(1,1,7,7-tetramethyljulolidin-9-yl)ethenyl]-4H-pyran (abbreviation: DCJTI), magnesium phthalocyanine, magnesium porphyrin, phthalocyanine, or the like is are preferable.

Note that the first electrode 101 and the second electrode 102 may have structures similar to those described above in Embodiment 2.

Further, in Embodiment 5, as illustrated in FIG. 1, the hole-inject layer 111, the hole-transport layer 112, the electron-transport layer 114, and the electron-inject layer 115 are provided. As to these layers, the structures of the respective layers described above in Embodiment 2 may be applied. However, these layers are not necessarily provided and may be provided as appropriate according to element characteristics.

By using any of the organometallic complexes of the present invention as a sensitizer, the foregoing light-emitting element can emit light highly efficiently.

Embodiment 6

In Embodiment 6, a light-emitting device fabricated using the organometallic complex of the present invention will be described.

Figure 4A:
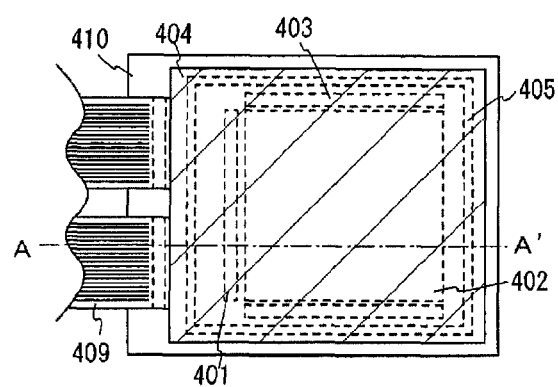
FIGS. 4A and 4B illustrate a light-emitting device according to an embodiment of the present invention.
Figure 4B:
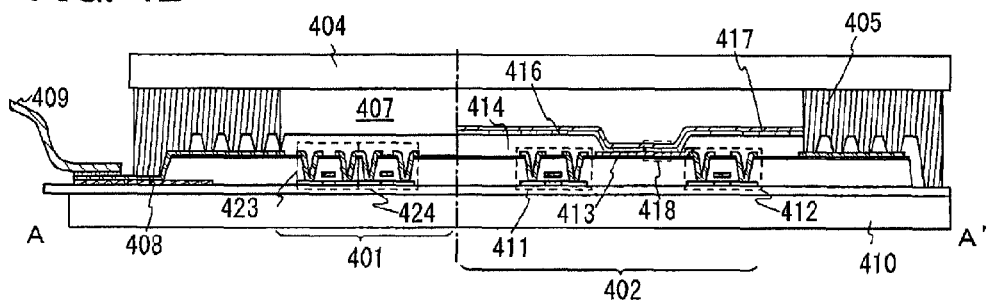

In Embodiment 6, a light-emitting device fabricated using any of the organometallic complexes of the present invention will be described with reference to FIGS. 4A and 4B. Note that FIG. 4A is a top view illustrating the light-emitting device, and FIG. 4B is a sectional view taken along the section A-A' of FIG. 4A. A source side driver circuit is denoted by reference numerals 401, 402 and 403, which are shown by a dotted line; denote a driver circuit portion (a source side driver circuit), a pixel portion, and a driver circuit portion (a gate driver circuit), respectively. Reference numeral 404 denotes a sealing substrate; reference numeral 405 denotes a sealant; and an inner side region enclosed by the sealant 405 is a space 407.

Note that a lead wiring 408 is a wiring for transmitting signals that are to be inputted to the source side driver circuit 401 and the gate side driver circuit 403, and receives a video signal, a clock signal, a start signal, a reset signal, and the like from a flexible printed circuit (FPC) 409 which serves as an external input terminal. Although only the FPCs are illustrated, printed wiring boards (PWBs) may be attached to the FPCs. The light-emitting device according to the present invention includes not only a light-emitting device body but also a state in which an FPC or a PWB is attached thereto.

Next, a sectional structure of the light-emitting device will be described using FIG. 4B. Although the driver circuit portions and the pixel portion 402 having a plurality of pixels are formed over a substrate 410, the source side driver circuit 401 which is the driver circuit portion and one of the plurality of pixels in the pixel portion 402 are illustrated here.

Note that as the source side driver circuit 401, a CMOS circuit which is obtained by combining an n-channel TFT 423 and a p-channel TFT 424 is formed. Further, a TFT for forming the driver circuit may be formed using a known CMOS circuit, a PMOS circuit, or an NMOS circuit. Although a driver integration type in which a driver circuit is formed over a substrate is described in Embodiment 6, a driver circuit is not necessarily formed over a substrate and can be formed outside a substrate.

The pixel portion 402 includes a plurality of pixels having a switching TFT 411, a current control TFT 412, and a first electrode 413 electrically connected to a drain of the current control TFT 412. An insulator 414 is formed to cover an end portion of the first electrode 413. Here, the insulator 614 is formed using a positive photosensitive acrylic resin film.

The insulator 414 is formed so as to have a curved surface having curvature at an upper end portion or a lower end portion thereof in order to obtain favorable coverage. For example, when positive type photosensitive acrylic is used as a material for the insulator 414, the insulator 414 preferably has a curved surface with a curvature radius (0.2 to 3 µm) only as the upper end. Alternatively, as the insulator 614, either a negative type which becomes insoluble in an etchant by light or a positive type which becomes soluble in an etchant by light can be used as the insulator 414.

Over the first electrode 413, a layer 416 including a light-emitting substance and a second electrode 417 are formed. Here, as a material for forming the first electrode 413 functioning as the anode, it is preferable to use a material having a high work function. For example, the first electrode 413 can be formed using a stack of a titanium nitride film and a film containing aluminum as its main component; a three-layer structure of a titanium nitride film, a film containing aluminum as its main component, and another titanium nitride film; or the like, as well as a single-layer film such as an indium tin oxide (ITO) film, an indium tin oxide film containing silicon, an indium zinc oxide (IZO) film, a titanium nitride film, a chromium film, a tungsten film, a Zn film, or a Pt film. Note that with a stack structure, the first electrode 413 has low resistance as a wiring, forms a favorable ohmic contact, and can serve as an anode.

The layer 416 including a light-emitting substance can be formed by an evaporation method using an evaporation mask. Since any of the organometallic complexes of the present invention has high affinity with a solvent, the layer 416 including a light-emitting substance can be formed, alternatively, by a wet method such as an inkjet method or a spin coating method.

The layer 416 including a light-emitting substance includes any of the organometallic complexes of the present invention, described in Embodiment 1. As a material that is to be combined therewith, a low molecular material, an oligomer, a dendrimer, or a high molecular material may be used. Further, as the layer including a light-emitting substance, although a single layer of an organic compound or a stack thereof is generally used, a structure may also be employed in which an organic compound film includes an inorganic compound is used, according to the present invention.

Furthermore, as a material used for the second electrode 417 which is to be formed over the layer 416 including a light-emitting substance, a material having a low work function (e.g., Al, Ag, Li, Ca, or an alloy or a compound of them, such as MgAg, MgIn, AlLi, LiF, $CaF_2$, calcium nitride, or calcium fluoride) is preferably used. Note that in the case where light emitted from the layer 416 including a light-emitting substance is transmitted through the second electrode 417 which serves as a cathode, a stack of a metal thin film with reduced film thickness and a transparent conductive film (formed using an indium oxide-tin oxide alloy (ITO), an indium oxide-zinc oxide alloy ($In_2O_3$—ZnO), zinc oxide (ZnO), or the like) is preferably used as the second electrode 417.

Attachment of the sealing substrate 404 to the substrate 410 with the sealant 405 makes a structure in which a light-emitting element 418 is provided in the space 407 surrounded by the substrate 410, the sealing substrate 404, and the sealant 405. Note that the space 407 may be filled with an inert gas (e.g., nitrogen or argon) or with the sealant 405.

Note that as the sealant 405, an epoxy-based resin is preferably used. In addition, it is preferable to use a material that allows permeation of moisture or oxygen as little as possible. As the sealing substrate 404, a plastic substrate made of fiberglass-reinforced plastics (FRP), polyvinyl fluoride (PVF), polyester, an acrylic resin, or the like can be used besides a glass substrate or a quartz substrate.

In the above-described manner, a light-emitting device fabricated using any of the organometallic complexes of the present invention can be obtained.

A light-emitting device of the present invention can have favorable characteristics since any of the organometallic complexes described in Embodiment 1 is used for the light-emitting device. Specifically, since a light-emitting element with high emission efficiency is included, a light-emitting device that has reduced power consumption and can be driven for a long time can be obtained. Further, since red light emission with high luminous efficiency can be realized, a light-emitting device with reduced power consumption and excellent color reproducibility, which is suitable for a full-color display, can be obtained.

Figure 5A:
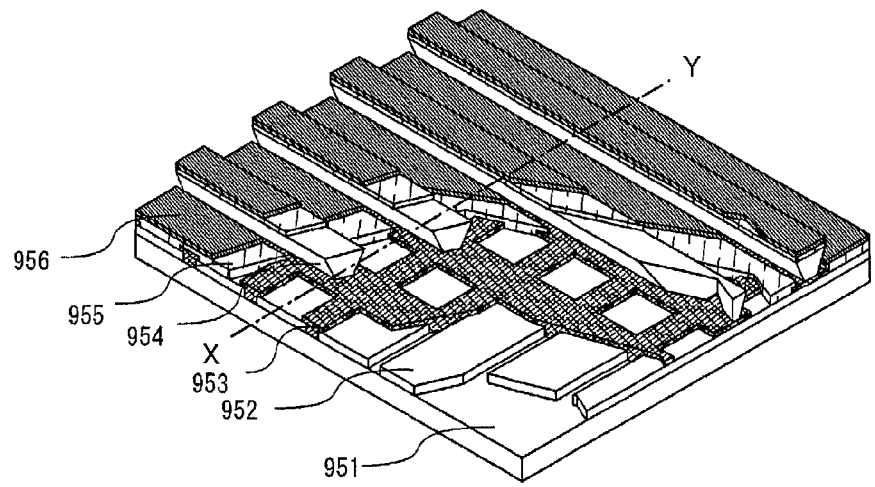
FIGS. 5A and 5B illustrate a light-emitting device according to an embodiment of the present invention.
Figure 5B:
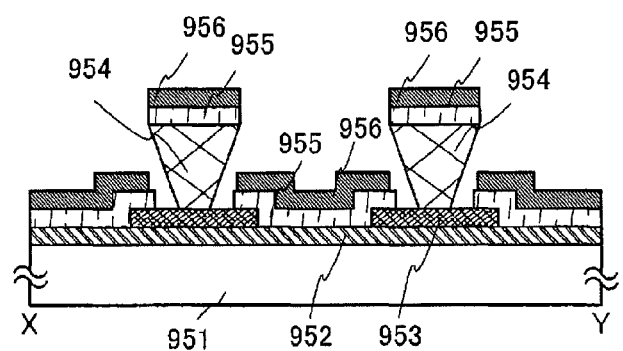

Although an active matrix light-emitting device which controls driving of a light-emitting element with a transistor is described above, the light-emitting device may be a passive matrix light-emitting device. FIGS. 5A and 5B illustrate a passive matrix image display device fabricated according to the present invention. Note that FIG. 5A is a perspective view illustrating the passive matrix image display device and FIG. 5B is a cross sectional view of FIG. 5A taken along a line X-Y. In FIGS. 5A and 5B, an electrode 952 and an electrode 956 are provided over a substrate 951, and a layer 955 including a light-emitting substance is provided between the electrodes 952 and 956. The edge of the electrode 952 is covered with an insulating layer 953. A partition wall layer 954 is provided on the insulating layer 953.

The sidewalls of the partition wall layer 954 are aslope so that a distance between both sidewalls is gradually narrowed toward the surface of the substrate. That is, a cross section in the direction of a narrow side of the partition wall layer 954 has a trapezoidal shape, and a lower side (which faces a surface of the insulating layer 953 and is in contact with the insulating layer 953) is shorter than an upper side (which faces the surface of the insulating layer 953 and is not in contact with the insulating layer 953). By providing the partition wall layer 954 in this manner, defects of the light-emitting element due to static charge and the like can be prevented.

Embodiment 7

In Embodiment 7, electronic devices of the present invention each including the light-emitting device described in Embodiment 6 will be described. The electronic devices of the present invention each have a display portion that includes any of the organometallic complexes described in Embodiment 1 and thus has high emission efficiency and reduced power consumption, can be driven for a long time, and has excellent color reproducibility.

As examples of the electronic devices each including a light-emitting element fabricated using any of the organometallic complexes of the present invention, there are televisions, cameras such as video cameras and digital cameras, goggle type displays, navigation systems, audio replay devices (e.g., car audio systems and audio systems), computers, game machines, portable information terminals (e.g., mobile computers, cellular phones, portable game machines, and electronic book readers), image replay devices in which a recording medium is provided (devices that are capable of replaying recording media such as digital versatile discs (DVDs) and equipped with a display device that can display an image), and the like. Specific examples of these electronic device are illustrated in FIGS. 6A to 6D.

Figure 6A:
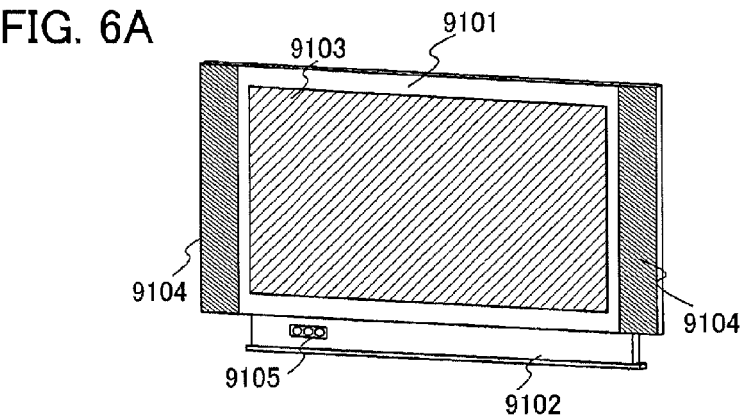
FIGS. 6A to 6D illustrate electronic devices according to an embodiment of the present invention.

FIG. 6A illustrates a television set according to the present invention, which includes a housing 9101, a supporting base 9102, a display portion 9103, a speaker portion 9104, a video input terminal 9105, and the like. In this television set, the display portion 9103 has light-emitting elements similar to those described in Embodiments 2 to 5 which are arranged in matrix. The features of the light-emitting elements are high emission efficiency and excellent color reproducibility. The display portion 9103 including the light-emitting elements has similar features and enables the television set to exhibit light emission with high luminance and a decrease in power consumption. Accordingly, the television set according to the present invention, which achieves lower power consumption and higher image quality, can be provided as a product that is suitable for any residential environment.

Figure 6B:
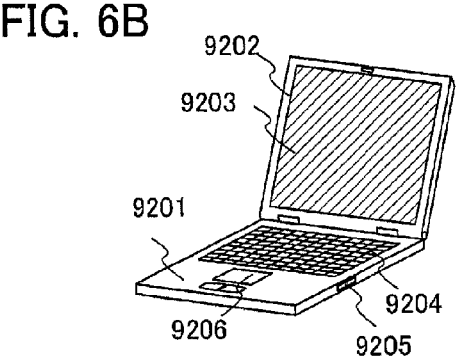

FIG. 6B illustrates a computer according to the present invention, which includes a main body 9201, a housing 9202, a display portion 9203, a keyboard 9204, an external connection port 9205, a pointing device 9206, and the like. In this computer, the display portion 9203 has light-emitting elements similar to those described in Embodiments 2 to 5, and the light-emitting elements are arranged in matrix. In this computer, the display portion 9203 has light-emitting elements similar to those described in Embodiments 2 to 5 which are arranged in matrix. The features of the light-emitting elements are high emission efficiency and excellent color reproducibility. The display portion 9203 including the light-emitting elements has similar features to achieve light emission with high luminance and a decrease in power consumption. Accordingly, the computer according to the present invention, which achieves lower power consumption and higher image quality, can be provided as a product that is suitable for the environment.

Figure 6C:
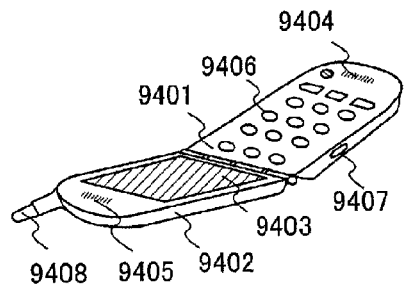

FIG. 6C illustrates a cellular phone according to the present invention, which includes a main body 9401, a housing 9402, a display portion 9403, an audio input portion 9404, an audio output portion 9405, an operation key 9406, an external connection port 9407, an antenna 9408, and the like. In this cellular phone, the display portion 9403 has light-emitting elements similar to those described in Embodiments 2 to 5 which are arranged in matrix. The features of the light-emitting elements are high emission efficiency and excellent color reproducibility. The display portion 9403 including the light-emitting elements has similar features to achieve light emission with high luminance and a decrease in power consumption. Accordingly, the cellular phone according to the present invention, which achieves lower power consumption and higher image quality, can be provided as a product that is suitable for portable use.

Figure 6D:
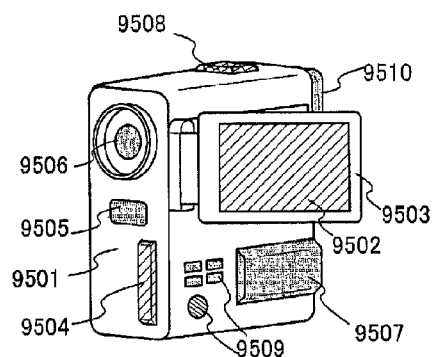

FIG. 6D illustrates a camera according to the present invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In this camera, the display portion 9502 has light-emitting elements similar to those described in Embodiments 2 to 5 which are arranged in matrix. The features of the light-emitting elements are that they have high emission efficiency, can be driven for a long time, and have excellent color reproducibility. The display portion 9502 including the light-emitting elements has similar features to achieve light emission with high luminance and a decrease in power consumption. Accordingly, the camera according to the present invention, which achieves lower power consumption and higher image quality, can be provided as a product that is suitable for portable use.

As described above, the applicable range of the light-emitting device of the present invention is wide so that the light-emitting device can be applied to electronic devices in various fields. By using any of the organometallic complexes of the present invention, electronic devices each having a display portion that has high emission efficiency, can be driven for a long time, and has reduced power consumption and excellent color reproducibility can be provided.

Further, the light-emitting device of the present invention can also be used as a lighting apparatus. One embodiment in which the light-emitting element of the present invention is used as a lighting apparatus will be described with reference to FIG. 7.

Figure 7:
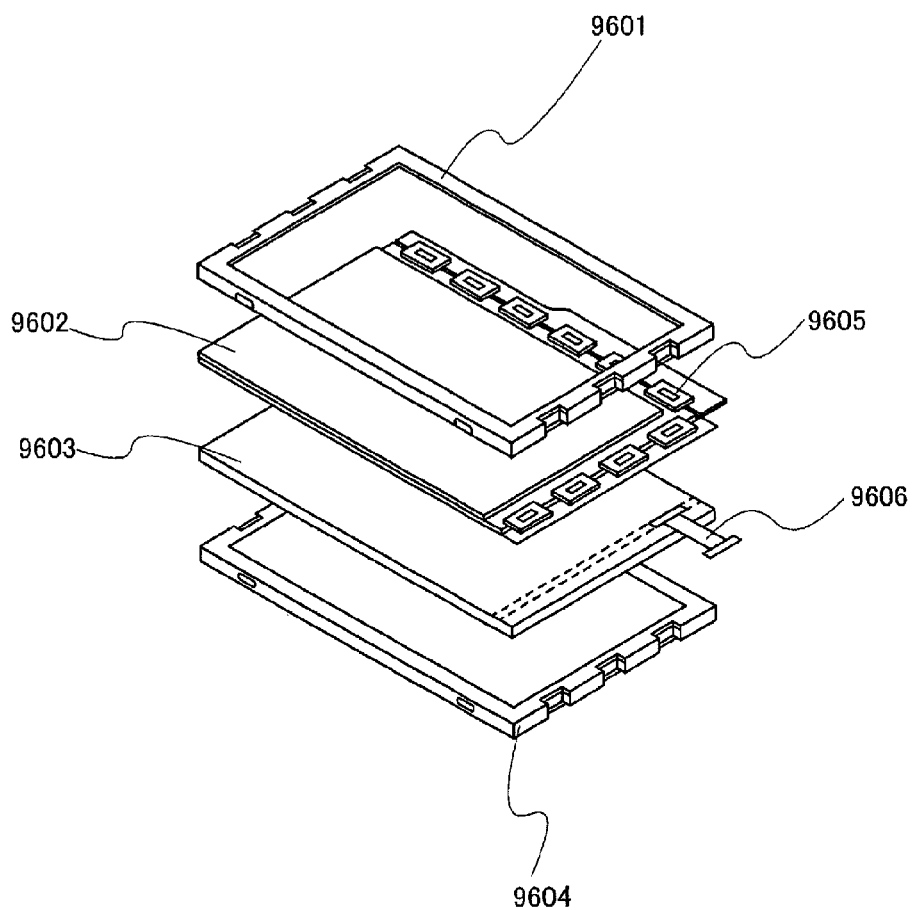
FIG. 7 illustrates an electronic device according to an embodiment of the present invention.

FIG. 7 is an example of a liquid crystal display device in which the light-emitting device of the present invention is used as a backlight. The liquid crystal display device illustrated in FIG. 7 includes a chassis 9601, a liquid crystal layer 9602, a backlight 9603, and a chassis 9604, and the liquid crystal layer 9602 is connected to a driver IC 9605. The light-emitting device of the present invention is used as the backlight 9603, and a current is supplied through a terminal 9606.

By using the light-emitting device of the present invention as the backlight of the liquid crystal display device, a backlight with high emission efficiency and reduced power consumption can be obtained. The light-emitting device of the invention is a plane emission type lighting apparatus, and can have a large area. Therefore, the backlight can have large area, and a liquid crystal display device having a large area can be obtained. Furthermore, since the light-emitting device of the invention has a thin shape and reduced power consumption, a thin shape and reduced power consumption of a display device can also be achieved. Further, since the light-emitting device of the present invention can exhibit light emission with high luminance, a liquid crystal display device using the light-emitting device of the present invention can also exhibit light emission with high luminance.

Figure 8:
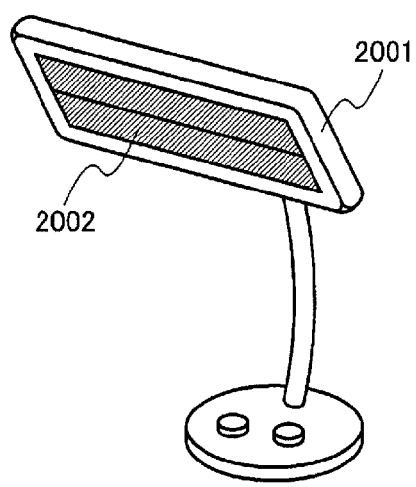
FIG. 8 illustrates a lighting apparatus according to an embodiment of the present invention.

FIG. 8 illustrates an example in which the light-emitting device according to the present invention is used as a table lamp, which is a lighting apparatus. A table lamp illustrated in FIG. 8 has a chassis 2001 and a light source 2002, and the light-emitting device of the present invention is used as the light source 2002. Since the light-emitting device of the present invention has high emission efficiency, can be driven for a long time, and has reduced power consumption, the table lamp also has high emission efficiency, can be driven for a long time, and has reduced power consumption.

Figure 9:
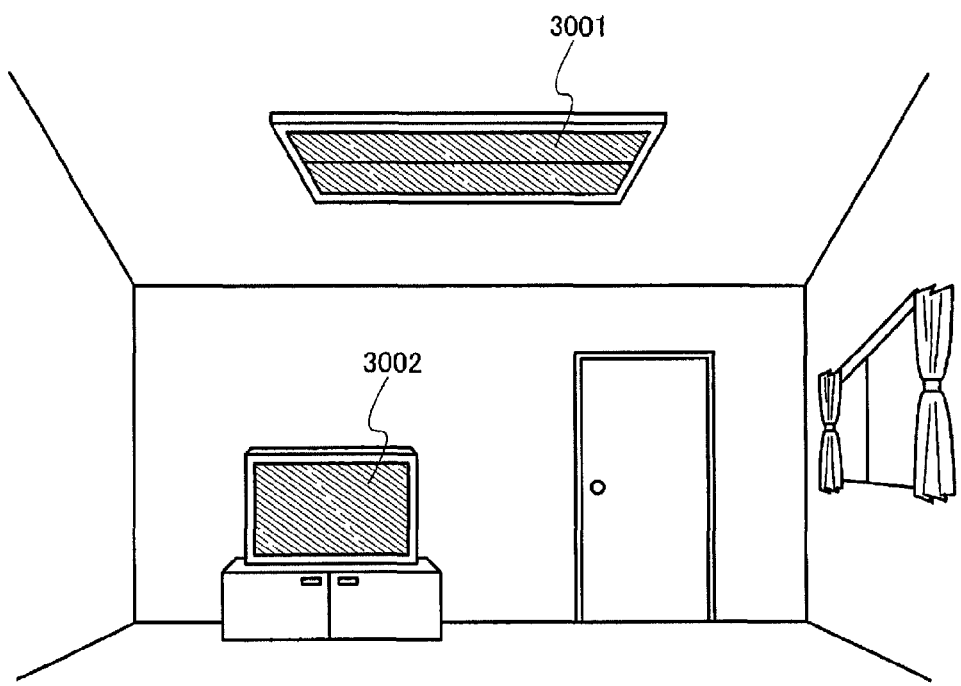
FIG. 9 illustrates a lighting apparatus according to an embodiment of the present invention.

FIG. 9 illustrates an example of using the light-emitting device to which the present invention is applied as an indoor lighting apparatus 3001.

Since the light-emitting device of the present invention can also have a large area, the light-emitting device of the present invention can be used as a lighting apparatus having a large emission area. Further, since the light-emitting device of the present invention has a thin shape and reduced power consumption, the light-emitting device of the present invention can be used as a lighting apparatus having a thin shape and consuming low power. A television set relating to the present invention as illustrated in FIG. 6A is placed in a room where the light-emitting device to which the present invention is applied is used as the indoor lighting apparatus 3001. Thus, public broadcasting and movies can be watched. In such the case, since both of the devices have reduced power consumption, a powerful image can be watched in a bright room without concern about electricity charges.

Example 1

⟨⟨Synthesis Example 1⟩⟩

In Synthesis Example 1, a synthesis example of the organometallic complex of the present invention which is represented by the structural formula (4) in Embodiment 1, (acetylacetonato)bis{2-(4-tert-butylphenyl)-dibenzo[f,h]quinoxalinato}iridium(III) (abbreviation: [Ir(dbq-tBuP)$_2$(acac)]), will be specifically described.

⟨Step 1: Synthesis of 2-(4-tert-Butylphenyl)-dibenzo[f,h]quinoxaline (Abbreviation: Hdbq-tBuP)⟩

First, 0.31 g of magnesium and 3 mL of tetrahydrofuran (abbreviation: THF) were suspended in a nitrogen atmosphere, and a small amount of 1,2-dibromoethane was added thereto. Then, a mixed solution in which 2.69 g of 1-bromo-4-tert-butylbenzene was dissolved in 12 mL of THF was dripped, and the mixture was stirred while being heated under reflux for 1 hour; thus, a Grignard reagent was prepared. To the prepared Grignard reagent were added 15 mL of THF and 2.64 g of dibenzo[f,h]quinoxaline, and the mixture was stirred while being heated under reflux for 24 hours. To this mixture was added water and then dilute hydrochloric acid, and the organic layer was extracted with dichloromethane. The obtained organic layer was dried over anhydrous magnesium sulfate. Then, the resulting solution was filtered. The solvent of this solution was distilled off. The resulting residue was purified by silica gel column chromatography which uses dichloromethane as a developing solvent. By recrystallization from ethyl acetate, Hdbq-tBuP which was the object of the synthesis was obtained (as a pale red powder in a yield of 10%). The synthesis scheme of Step 1 is illustrated in the following (a″-1).

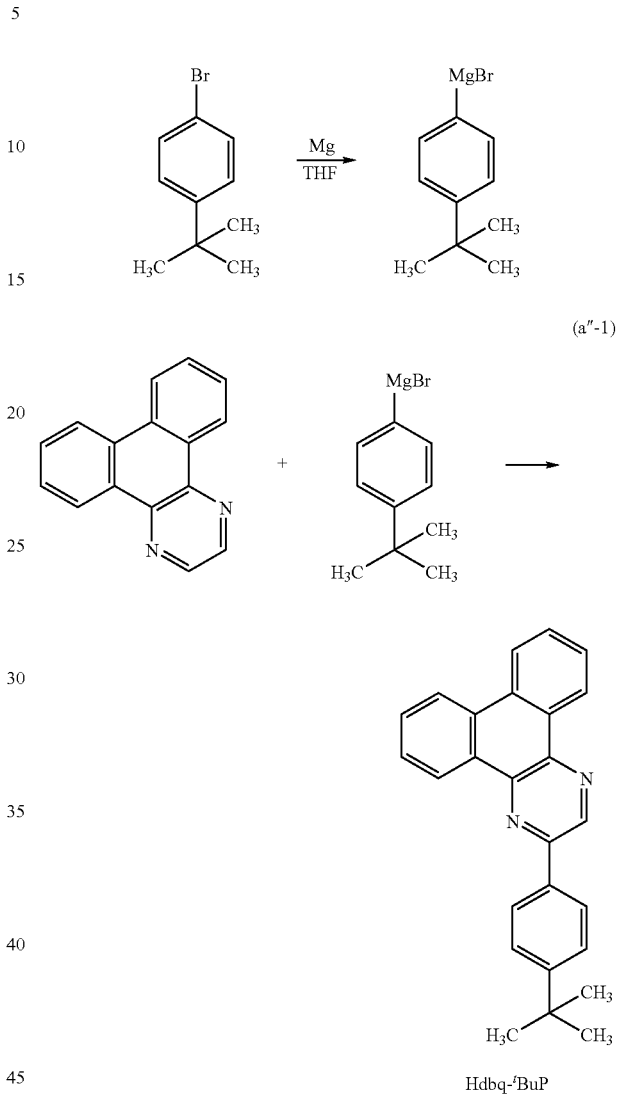

(a″-1)

⟨Step 2: Synthesis of Di-μ-chloro-bis[bis{2-(4-tert-butylphenyl)-dibenzo[f,h]quinoxalinato iridium(III)] (Abbreviation: [Ir(dbq-tBuP)$_2$Cl]$_2$)⟩

In a recovery flask equipped with a reflux pipe were put 3 mL of 2-ethoxyethanol, 1 mL of water, 0.10 g of Hdbq-tBuP obtained in the above Step 1, and 0.04 g of iridium chloride hydrate (IrCl$_3$·H$_2$O) (produced by Sigma-Aldrich Corp.). The atmosphere in the flask was substituted with argon. Then, the mixture was irradiated with a microwave (2.45 GHz, 100 W) for 2 hours so as to react. A red powder precipitated from the reaction solution was collected by filtration, and the residue was washed with ethanol to give a dinuclear complex [Ir(dbq-tBuP)$_2$Cl]$_2$ (in a yield of 37%). Note that for the microwave irradiation, a microwave synthesis system (Discovery, produced by CEM Corporation) was used. In addition, the synthesis scheme of Step 2 is illustrated in the following (b-1).

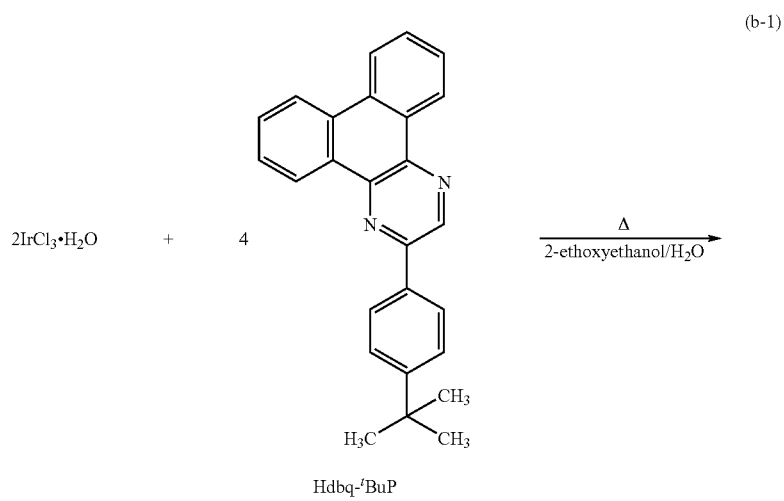

(b-1)

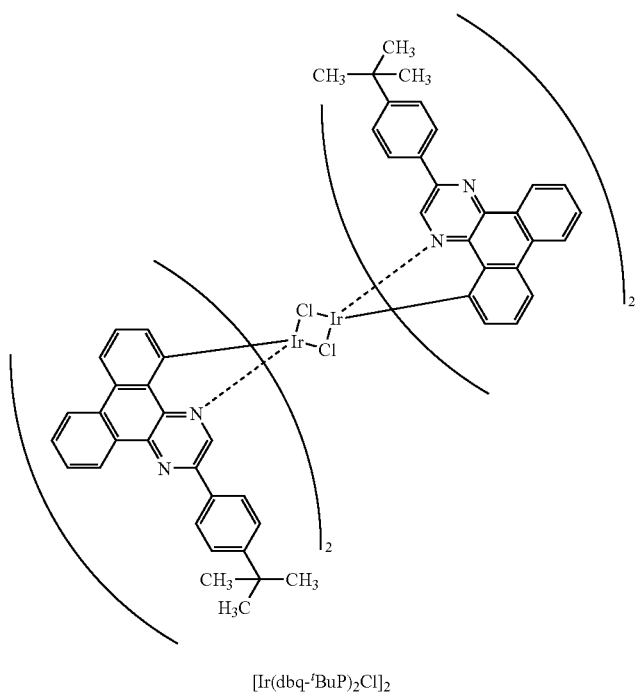

‹Step 3: Synthesis of (acetylacetonato)bis{2-(4-tert-butylphenyl)-dibenzo[f,h]quinoxalinato}iridium(III) (Abbreviation: [Ir(dbq-tBuP)₂(acac)])›

In a recovery flask equipped with a reflux pipe were put 10 mL of 2-ethoxyethanol, 0.43 g of the dinuclear complex, [Ir(dbq-tBuP)₂Cl]₂, which was obtained in the above Step 2, and 0.084 g of sodium acetylacetonato hydrate (Na(CH₃COCHCOCH₃)·XH₂O). The atmosphere in the flask was substituted with argon. Then, the mixture was irradiated with a microwave (2.45 GHz, 100) for 45 minutes so as to react. The reaction solution was filtered. The residue obtained was dissolved in dichloromethane, and an insoluble portion was removed by filtration. By recrystallization from a mixed solvent of ethyl acetate and dichloromethane, an organometallic complex of the present invention, [Ir(dbq-tBuP)₂(acac)], was obtained as a red powder (in a yield of 4%). The synthesis scheme of Step 3 is illustrated in the following (c-1).

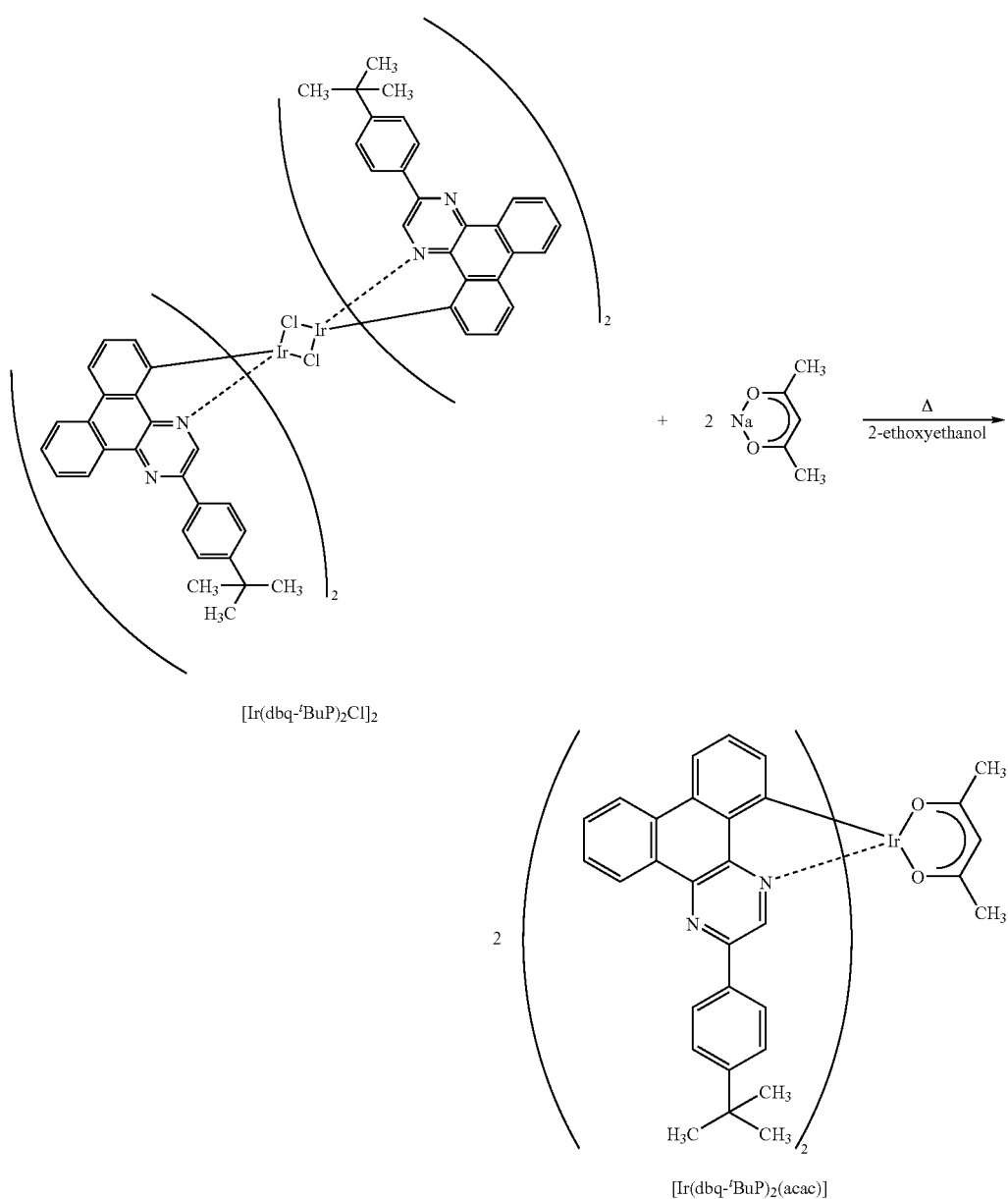

Figure 10:
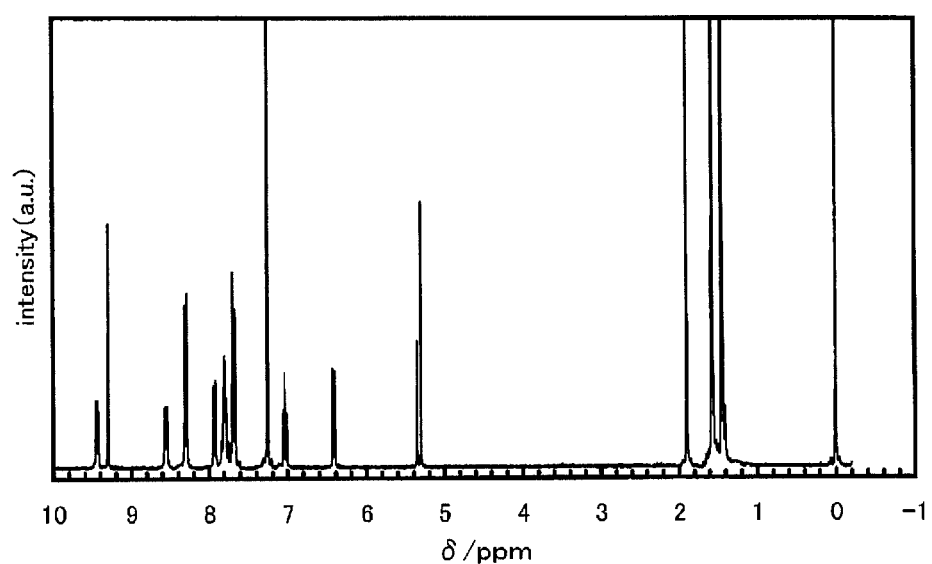
FIG. 10 is a $^1$H-NMR chart of (acetylacetonato)bis{2-(4-tert-butylphenyl)-dibenzo[f,h]quinoxalinato}iridium(III) synthesized in Example 1.

Note that results of the analysis in which the red powder obtained in the above Step 3 was analyzed by nuclear magnetic resonance spectrometry ($^1$H-NMR) are given below. In addition, FIG. 10 shows a $^1$H-NMR chart. These results demonstrate that the organometallic complex of the present invention which is represented by the structural formula (4), [Ir(dbq-tBuP)$_2$(acac)], was obtained in Synthesis Example 1. $^1$H NMR. δ (CDCl$_3$): 1.44 (s, 18H), 1.89 (s, 6H), 5.35 (s, 1H), 6.42 (d, 2H), 7.04 (t, 2H), 7.68 (d, 4H), 7.79 (m, 4H), 7.93 (d, 2H), 8.30 (d, 4H), 8.55 (d, 2H), 9.30 (s, 2H), 9.44 (dd, 2H).

Figure 11:
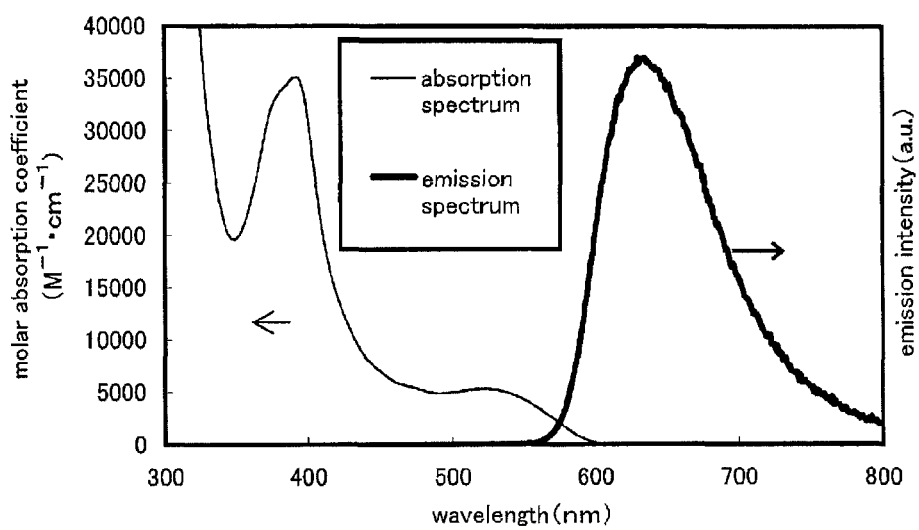
FIG. 11 shows an ultraviolet-visible absorption spectrum and an emission spectrum of a dichloromethane solution of (acetylacetonato)bis{2-(4-tert-butylphenyl)-dibenzo[f,h]quinoxalinato}iridium(III) synthesized in Example 1.

Next, [Ir(dbq-tBuP)$_2$(acac)] was analyzed by an ultraviolet-visible (UV) absorption spectroscopy. The UV spectrum was measured with an ultraviolet-visible spectrophotometer (V550, produced by JASCO Corporation). The measurement was conducted by using a dichloromethane solution (0.058 mmol/L) at room temperature. Further, an emission spectrum of [Ir(dbq-tBuP)$_2$(acac)] was measured with a fluorescence spectrophotometer (FS920, produced by Hamamatsu Photonics Corporation). The measurement was conducted by using a degassed dichloromethane solution (0.35 mmol/L) at room temperature. FIG. 11 shows the measurement results. The horizontal axis represents wavelength and the vertical axis represents molar absorption coefficient and emission intensity.

As shown in FIG. 11, the organometallic complex of the present invention, [Ir(dbq-tBuP)$_2$(acac)], has a peak of emission spectrum at 634 nm, and red light emission from the dichloromethane solution was observed.

Further, like usual Ir complexes that undergo ortho-metalation, broad absorption was observed on the longer wavelength side of the absorption spectrum. The absorption in the longer wavelength region indicates the existence of metal-to-ligand charge transfer (MLCT transfer) from Ir to a ligand. It is thought that the absorption in the region at more than 500 to 600 nm, in particular, results from the triplet MLCT transfer. Therefore, [Ir(dbq-tBuP)₂(acac)] is a material capable of direct excitation to a triplet excited state or intersystem crossing from a singlet excited state to a triplet excited state.

Considering the existence of the above absorption, red light emission having a peak at 634 nm is phosphorescence from a triplet excited state. Thus, by applying [Ir(dbq-tBuP)₂(acac)], which easily exhibits light emission (phosphorescence) from a triplet excited state, to a light-emitting element, the light-emitting element with high efficiency is provided.

Next, results of solubility determination of [Ir(dbq-tBuP)₂(acac)] are shown in the table.

TABLE 1

| Solvent | Ir(dbq-tBuP)₂(acac) Solubility x (g/L) |
| --- | --- |
| Ethanol | x < 0.6 |
| Isopropyl alcohol | x < 0.6 |
| 2-Ethoxyethanol | 0.6 ≤ x < 0.9 |
| 1,4-Dioxane | 0.9 ≤ x < 1.2 |
| Chloroform | 1.2 ≤ x |
| Toluene | 1.2 ≤ x |

It is confirmed that Ir(dbq-tBuP)₂(acac) can be dissolved in each of 2-ethoxyethanol, 1,4-dioxane, chloroform, and toluene. In particular, it is confirmed that a solubility of 1.2 g/liter or more in each of chloroform and toluene is exhibited; thus, Ir(dbq-tBuP)₂(acac) can be readily dissolved in each of chloroform and toluene.

Example 2

⟨⟨Synthesis Example 2⟩⟩

In Synthesis Example 2, a synthesis example of the organometallic complex of the present invention which is represented by the structural formula (17) in Embodiment 1, (acetylacetonato)bis[2-(3-methylphenyl)-dibenzo[f,h]quinoxalinato)iridium(III) (abbreviation: [Ir(dbq-3MP)₂(acac)]), will be specifically described.

⟨Step 1: Synthesis of Dibenzo[f,h]quinoxaline-1-oxide⟩

First, to a solution in which 1.36 g of dibenzo[f,h]quinoxaline was dissolved in 20 mL of dichloromethane was added 2.04 g of 3-chlorobenzoic acid (abbreviation: MCPBA) in a nitrogen atmosphere, followed by stirring at room temperature for 1 week. Water was added to this mixture, and the organic layer was extracted with dichloromethane. The obtained organic layer was washed with a saturated aqueous sodium hydrogen carbonate solution and dried over anhydrous magnesium sulfate. Then, the resulting solution was filtered. The solvent of this solution was distilled off. The resulting residue was purified by silica gel column chromatography which uses a mixed solvent of dichloromethane and ethyl acetate as a developing layer. By recrystallization from dichloromethane, the object of the synthesis was obtained (as a white powder in a yield of 51%). The synthesis scheme of Step 1 is illustrated in the following (a'''-2-1).

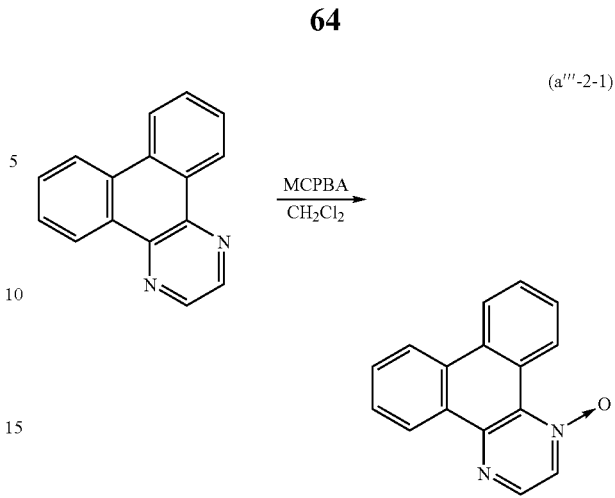

(a'''-2-1)

⟨Step 2: Synthesis of 2-Chloro-Dibenzo[f,h]Quinoxaline⟩

Next, 18 mL of phosphoryl chloride was dripped into 2.91 g of dibenzo[f,h]quinoxaline-1-oxide obtained in the above Step 1. This mixed solution was stirred while being heated under reflux for 1 hour. This mixed solution was poured into iced water, followed by addition of potassium carbonate so that the mixture was alkaline. This solution was filtered, and the obtained residue was washed with water and then methanol to give the object of the synthesis (as a pale yellow powder in a yield of 93%). The synthesis scheme of Step 2 is illustrated in the following (a'''-2-2).

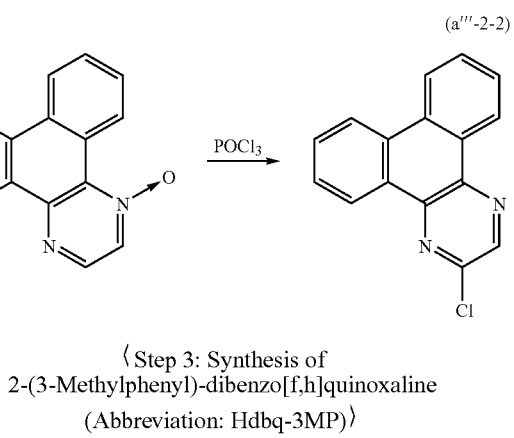

(a'''-2-2)

⟨Step 3: Synthesis of 2-(3-Methylphenyl)-dibenzo[f,h]quinoxaline (Abbreviation: Hdbq-3MP)⟩

In a recovery flask equipped with a reflux pipe were put 0.60 g of 2-chloro-dibenzo[f,h]quinoxaline obtained in the above Step 2, 0.33 g of 3-methylphenylboronic acid, 0.080 g of tetrakis(triphenylphosphine)palladium(0) (Pd(PPh₃)₄), 10 mL of toluene, 1.5 mL of ethanol, and 2.5 mL of a 2M aqueous potassium carbonate solution. The atmosphere in the flask was substituted with argon. Then, the mixture was irradiated with a microwave (2.45 GHz, 100 W) for 50 minutes so as to react. Dichloromethane was added to the reaction solution to extract the organic layer. The obtained organic layer was washed with water and dried over anhydrous magnesium sulfate. Then, the resulting solution was filtered. The solvent of this solution was distilled off. Then, the resulting residue was washed with ethanol to give the ligand which is the object of the synthesis, Hdbq-3MP (as a milky powder in a yield of 91%). The synthesis scheme of Step 3 is illustrated in (a'''-2-3) below. Note that for the microwave irradiation, a microwave synthesis system (Discovery, produced by CEM Corporation) was used.

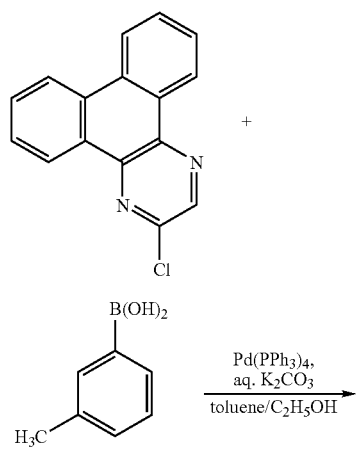

(a'''-2-3)

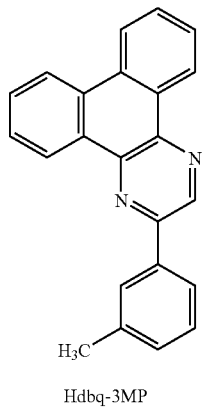

⟨Step 4: Synthesis of Di-μ-chloro-bis[bis{2-(3-methylphenyl)-dibenzo[f,h]quinoxalinato)iridium(III)] (Abbreviation: [Ir(dbq-3MP)₂Cl]₂)⟩

Next, in a recovery flask equipped with a reflux pipe were put 15 mL of 2-ethoxyethanol, 5 mL of water, 1.20 g of Hdbq-3MP obtained in the above Step 3, and 0.56 g of iridium chloride hydrate (IrCl₃.H₂O) (produced by Sigma-Aldrich Corp.). The atmosphere in the flask was substituted with argon. Then, the mixture was irradiated with a microwave (2.45 GHz, 100 W) for 4 hours and 20 minutes so as to react. An orange powder precipitated from the reaction solution was collected by filtration, and washed with ethanol, acetone, and then ether to give a dinuclear complex [Ir(dbq-3MP)₂Cl]₂ (in a yield of 95%). In addition, the synthesis scheme of Step 4 is shown in the following (b-2).

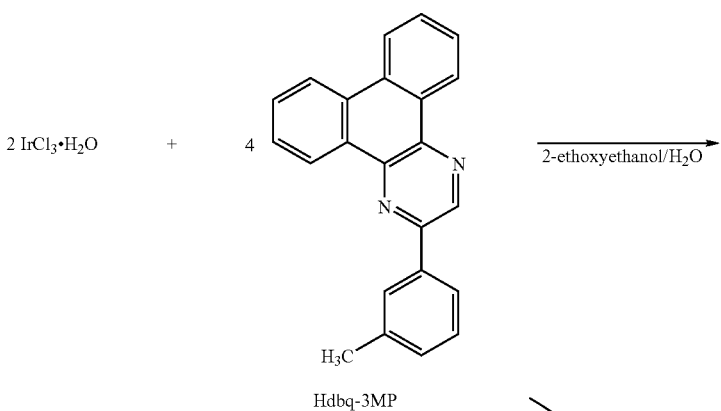

(b-2)

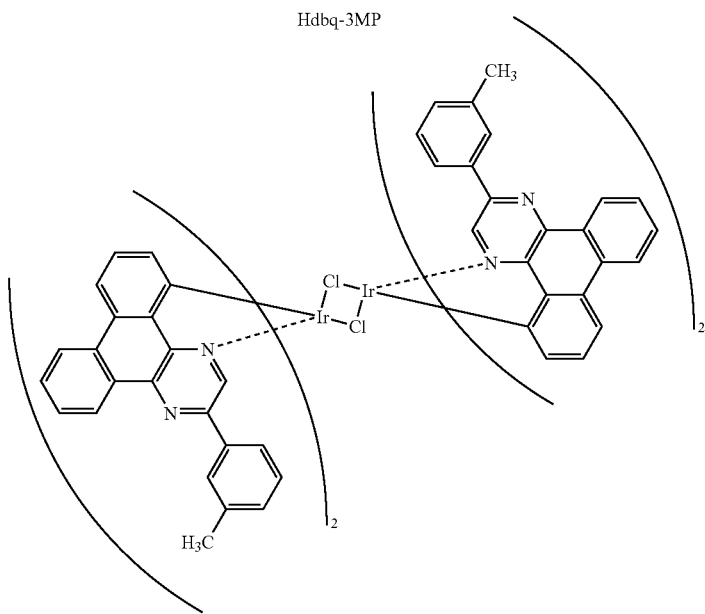

《Step 5: Synthesis of (Acetylacetonato)bis[2-(3-methylphenyl)-dibenzo[f,h]quinoxalinato)iridium (III) (Abbreviation: [Ir(dbq-3MP)₂(acac)])》

Figure 12:
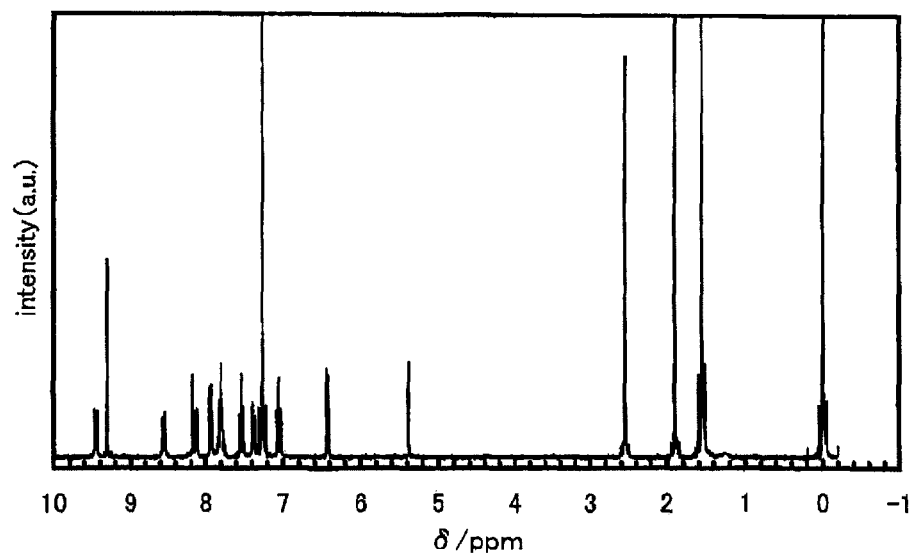
FIG. 12 is a $^1$H-NMR chart of Isomer I of an organometallic complex synthesized in Example 2.
Figure 13:
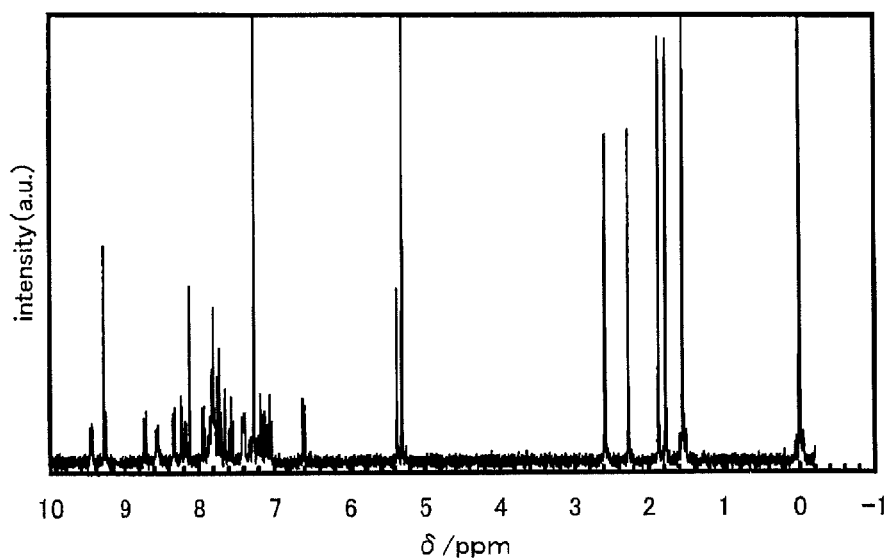
FIG. 13 is a $^1$H-NMR chart of Isomer II of the organometallic complex synthesized in Example 2.

Further, in a recovery flask equipped with a reflux pipe were put 20 mL of 2-ethoxyethanol, 1.55 g of the dinuclear complex, [Ir(dbq-3MP)₂Cl]₂, which was obtained in the above Step 4, and 0.33 g of sodium acetylacetonato hydrate (Na(CH₃COCHCOCH₃).XH₂O). The atmosphere in the flask was substituted with argon. Then, the mixture was irradiated with a microwave (2.45 GHz, 100 W) for 1 hour so as to react. The reaction solution was filtered. The residue obtained was dissolved in dichloromethane, followed by filtration. This filtrate was concentrated, dried, and hardened. The resulting residue was purified by column chromatography which uses dichloromethane as a developing solvent. By recrystallization from dichloromethane, the organometallic complex of the present invention, [Ir(dbq-3MP)₂(acac)], was obtained as two types of structural isomers (produced as red powders in a yield of 9% with the ratio of Isomer I to Isomer II being 1:2). The synthesis scheme of Step 5 is illustrated in the following (c-2).

addition, FIG. 12 shows a ¹H-NMR chart of Isomer I. FIG. 13 shows a ¹H-NMR chart of Isomer II. These results demonstrate that the organometallic complex of the present invention which is represented by the structural formula (17), [Ir(dbq-3MP)₂(acac)], was obtained in Synthesis Example 2.

¹H NMR of Isomer I. δ (CDCl₃): 1.90 (s, 6H), 2.55 (s, 6H), 5.38 (s, 1H), 6.43 (d, 2H), 7.05 (t, 2H), 7.38 (d, 2H), 7.53 (t, 2H), 7.80 (m, 4H), 7.94 (d, 2H), 8.13 (d, 2H), 8.18 (s, 2H), 8.56 (m, 2H), 9.30 (s, 2H), 9.45 (m, 2H).

¹H NMR of Isomer II. δ (CDCl₃): 1.78 (s, 3H), 1.87 (s, 3H), 2.28 (s, 3H), 2.58 (s, 3H), 5.37 (s, 1H), 6.61 (d, 1H), 7.11 (m, 2H), 7.39 (m, 2H), 7.56 (t, 1H), 7.65-7.96 (m, 8H), 7.96 (d, 1H), 8.12 (s, 1H), 8.18 (d, 1H), 8.24 (s, 1H), 8.33 (d, 1H), 8.56 (d, 1H), 8.72 (d, 1H), 9.29 (m, 2H), 9.46 (m, 1H).

Next, [Ir(dbq-3MP)₂(acac)] was analyzed by an ultraviolet-visible (UV) absorption spectroscopy. The UV spectrum was measured with an ultraviolet-visible spectrophotometer (V550, produced by JASCO Corporation). The measurement was conducted by using a dichloromethane solution (0.058 mmol/L) at room temperature. Further, an emission spectrum of [Ir(dbq-3MP)₂(acac)] was measured with a fluorescence spectrophotometer (FS920, produced by Hamamatsu Photo-

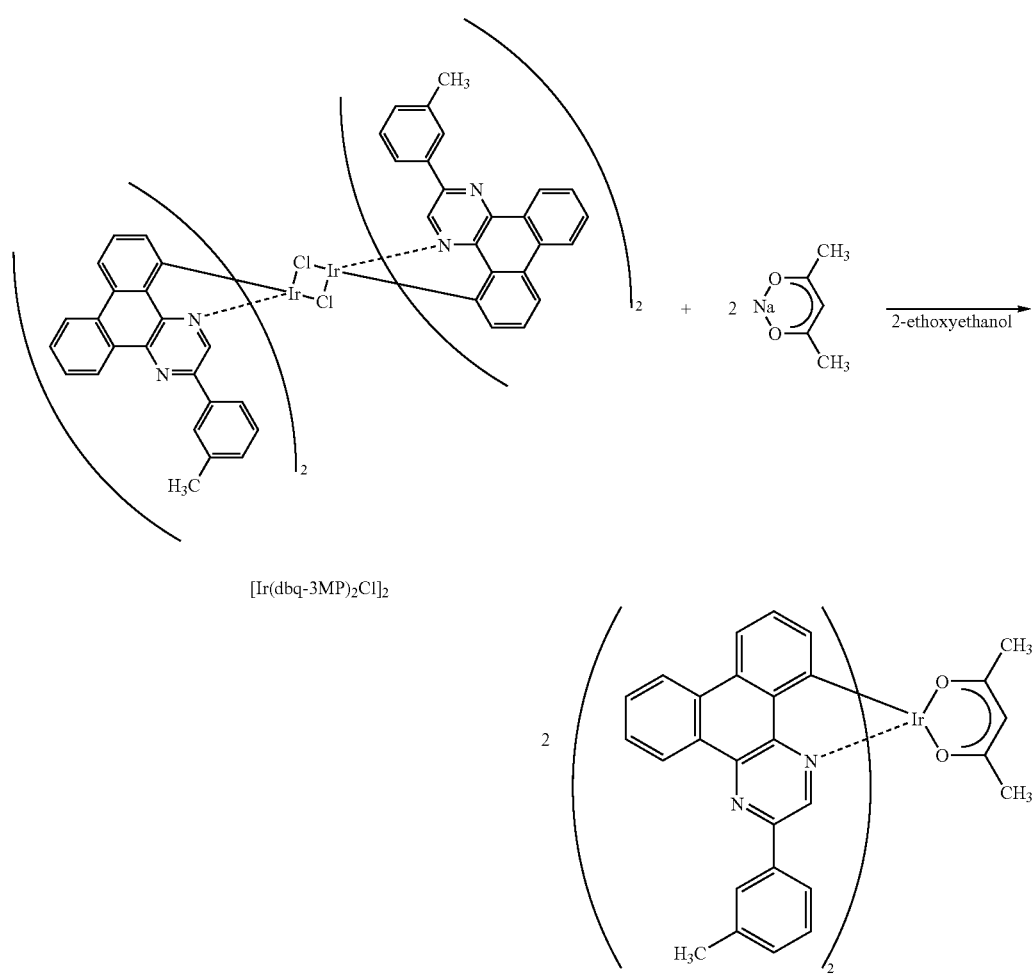

(c-2)

Figure 14:
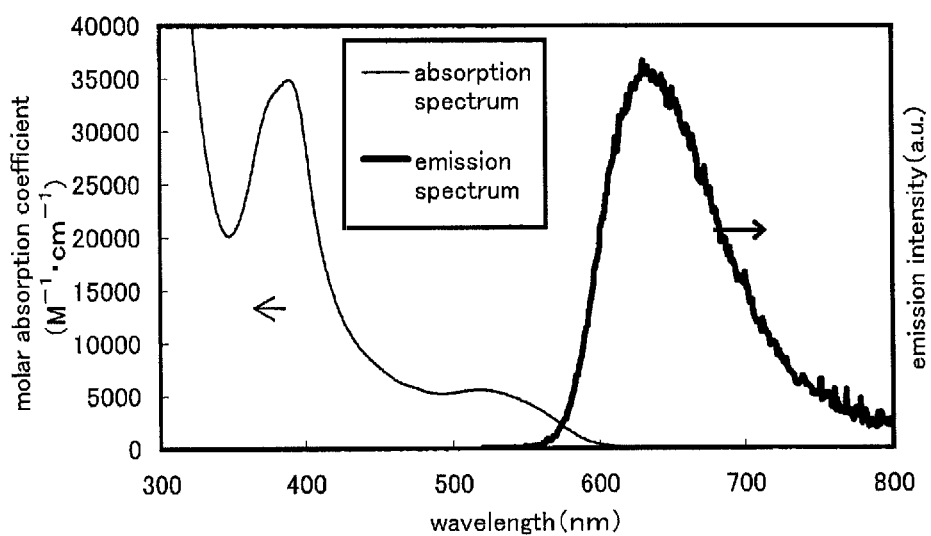
FIG. 14 shows an ultraviolet-visible absorption spectrum and an emission spectrum of a dichloromethane solution of Isomer I of the organometallic complex of the present invention, [Ir(dbq-3MP)$_2$(acac)].
Figure 15:
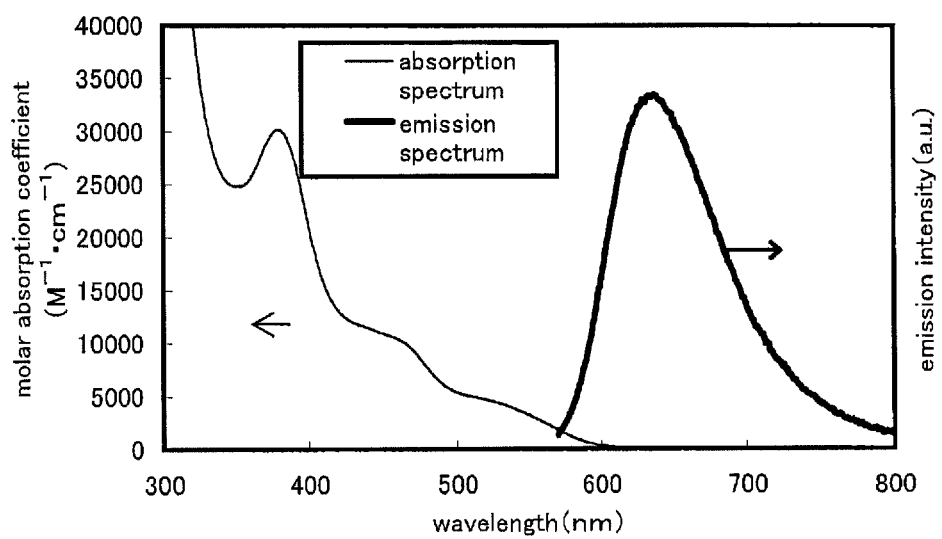
FIG. 15 shows an ultraviolet-visible absorption spectrum and an emission spectrum of a dichloromethane solution of Isomer II of the organometallic complex of the present invention, [Ir(dbq-3MP)$_2$(acac)].

Note that results of the analysis in which the red powders obtained in the above Step 5 were analyzed by nuclear magnetic resonance spectrometry (¹H-NMR) are given below. In nics Corporation). The measurement was conducted by using a degassed dichloromethane solution (0.35 mmol/L) at room temperature. FIG. 14 shows the measurement results of Isomer I. FIG. 15 shows the measurement results of Isomer II. The horizontal axis represents wavelength and the vertical axis represents molar absorption coefficient and emission intensity.

As illustrated in FIG. 14 and FIG. 15, each of the isomers of the organometallic complex of the present invention, [Ir(dbq-3MP)$_2$(acac)], has a peak of emission spectrum at about 640 nm, and red light emission from the dichloromethane solution was observed.

Further, like usual Ir complexes that undergo ortho-metalation, broad absorption was observed on the longer wavelength side of the absorption spectrum. The absorption in the longer wavelength region indicates the existence of metal-to-ligand charge transfer (MLCT transfer) from Ir to a ligand. It is thought that the absorption in the region at more than 500 to 600 nm, in particular, results from the triplet MLCT transfer. Therefore, [Ir(dbq-3MP)$_2$(acac)] is a material capable of direct excitation to a triplet excited state or intersystem crossing from a singlet excited state to a triplet excited state.

Considering the existence of the above absorption, red light emission having a peak at about 640 nm is phosphorescence from a triplet excited state. Thus, by applying [Ir(dbq-3MP)$_2$(acac)], which easily exhibits light emission (phosphorescence) from a triplet excited state, to a light-emitting element, the light-emitting element is expected to have high efficiency.

This application is based on Japanese Patent Application serial no. 2008-166035 filed with Japan Patent Office on Jun. 25, 2008, the entire contents of which are hereby incorporated by reference.

EXPLANATION OF REFERENCE

101: first electrode, 102: second electrode, 111: hole-inject layer, 112: hole-transport layer, 113: light-emitting layer, 114: electron-transport layer, 115: electron-inject layer, 201: first electrode, 202: second electrode, 211: hole-inject layer, 212: hole-transport layer, 213: first light-emitting layer, 214: separation layer, 215: second light-emitting layer, 216: electron-transport layer, 217: electron-inject layer, 301: first electrode, 302: second electrode, 311: hole-inject layer, 312: hole-transport layer, 313: first light-emitting layer, 314: electron-transport layer, 315: hole-transport layer, 316: second light-emitting layer, 317: electron-transport layer, 318: electron-inject layer, 321: N layer, 322: P layer, 401: source side driver circuit, 402: pixel portion, 403: gate side driver circuit, 404: sealing substrate, 405: sealant, 407: space, 408: wiring, 409: flexible printed circuit (FPC), 410: substrate, 411: switching TFT, 412: current control TFT, 413: first electrode, 414: insulator, 416: layer including light-emitting substance, 417: second electrode, 418: light-emitting element, 423: N-channel TFT, 424: P-channel TFT, 951: substrate, 952: electrode, 953: insulating layer, 954: partition layer, 955: layer including light-emitting substance, 956: electrode, 2001: chassis, 2002: light source, 3001: lighting apparatus, 3002: television set, 9101: chassis, 9102: supporting base, 9103: display portion, 9104: speaker portion, 9105: video input terminal, 9201: main body, 9202: chassis, 9203: display portion, 9204: keyboard, 9205: external connection port, 9206: pointing device, 9401: main body, 9402: chassis, 9403: display portion, 9404: audio input portion, 9405: audio output portion, 9406: operation key, 9407: external connection port, 9408: antenna, 9501: main body, 9502: display portion, 9503: chassis, 9504: external connection port, 9505: remote control receiving portion, 9506: image receiving portion, 9507: battery, 9508: audio input portion, 9509: operation key, 9510: eye piece portion, 9601: chassis, 9602: liquid crystal layer, 9603: backlight, 9604: chassis, 9605: driver IC, 9606: terminal.

The invention claimed is:

1. An organometallic complex having a structure represented by a formula (C-2)

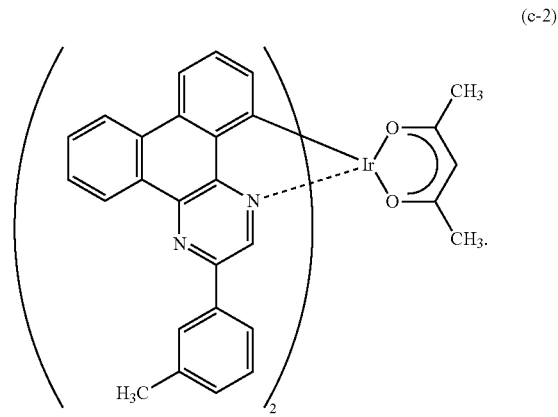

(c-2)

2. A light-emitting element comprising the organometallic complex according to claim 1.

3. A light-emitting device comprising a light-emitting element including the organometallic complex according to claim 1.

4. An electronic device comprising a display portion, wherein the display portion includes the light-emitting device according to claim 3.

* * * * *